US008086468B2

(12) United States Patent  (10) Patent No.: US 8,086,468 B2
Kim  (45) Date of Patent: Dec. 27, 2011

(54) METHOD FOR COMPUTERISING AND STANDARDIZING MEDICAL INFORMATION

(75) Inventor: Suhung-Gwon Kim, Seoul (KR)

(73) Assignee: EZ-Caretech Co., Ltd., Seoul (KR)

( * ) Notice: Subject to any disclaimer, the term of this patent is extended or adjusted under 35 U.S.C. 154(b) by 102 days.

(21) Appl. No.: 10/564,713

(22) PCT Filed: Jul. 13, 2004

(86) PCT No.: PCT/KR2004/001734
§ 371 (c)(1),
(2), (4) Date: Jul. 19, 2006

(87) PCT Pub. No.: WO2005/006235
PCT Pub. Date: Jan. 20, 2005

(65) Prior Publication Data
US 2007/0088559 A1  Apr. 19, 2007

(30) Foreign Application Priority Data

Jul. 14, 2003 (KR) .................. 10-2003-0047804

(51) Int. Cl.
*G06Q 10/00* (2006.01)
(52) U.S. Cl. ................................. 705/2; 705/3
(58) Field of Classification Search ............... 705/2–4; 600/300
See application file for complete search history.

(56) References Cited

U.S. PATENT DOCUMENTS

| 4,858,121 | A |   | 8/1989  | Barber et al. |
|-----------|---|---|---------|---------------|
| 5,823,948 | A | * | 10/1998 | Ross et al. ............ 600/300 |
| 5,935,060 | A |   | 8/1999  | Iliff |
| 5,991,731 | A |   | 11/1999 | Colon et al. |
| 6,047,259 | A | * | 4/2000  | Campbell et al. ............ 705/3 |
| 2001/0049610 | A1 |   | 12/2001 | Hazumi |
| 2002/0004727 | A1 |   | 1/2002  | Knaus et al. |
| 2002/0082868 | A1 | * | 6/2002  | Pories et al. ............ 705/3 |

FOREIGN PATENT DOCUMENTS

| EP | 0 625 759 B1 | 8/2001 |
| EP | 1 284 468    | 2/2003 |
| JP | 09-258803 A  | 10/1997 |
| JP | 10-0097582 A | 4/1998 |

(Continued)

OTHER PUBLICATIONS

Greenes, R.A.; "A Hierarchical Data Management Facility for Clinical Record Appplications", Nov. 1968, IEEE New York, NY, "Proceedings of the Annual Conference on Engineering in Medicine & Biology" vol. 10 p. 552.*

(Continued)

*Primary Examiner* — Vivek Koppikar
*Assistant Examiner* — Rajiv Raj
(74) *Attorney, Agent, or Firm* — Sterne, Kessler, Goldstein & Fox P.L.L.C.

(57) ABSTRACT

The present invention is to provide a method for computerizing and standardizing medical information, which can provide web screens through terminals to enable doctors, nurses, pharmacists, or the like to immediately online input and read a variety of information created upon treating and caring for patients in a hospital, and can standardize medical information input or represented through the web screens, such as various medical information, nursing information, medicine information and the like.

10 Claims, 21 Drawing Sheets

FOREIGN PATENT DOCUMENTS

| | | |
|---|---|---|
| JP | 2003-67485 | 3/2003 |
| KR | 2000-0063796 A | 11/2000 |
| KR | 2001-0109944 A | 12/2001 |
| KR | 2002-0071546 A | 9/2002 |
| KR | 2002-0089225 A | 11/2002 |
| KR | 2003-0000426 A | 1/2003 |
| KR | 2003-0009755 A | 2/2003 |
| KR | 2003-0025507 A | 3/2003 |
| WO | WO 01/15043 | 3/2001 |

OTHER PUBLICATIONS

International Search Report for International Patent Application No. PCT/KR2004/001408, mailed Aug. 19, 2004, Korean Intellectual Patent Office, Republic of Korea.

International Search Report for International Patent Application No. PCT/KR2004/001733, mailed Oct. 25, 2004, Korean Intellectual Patent Office, Republic of Korea.

International Search Report for International Patent Application No. PCT/KR2004/001734, mailed Oct. 25, 2004, Korean Intellectual Patent Office, Republic of Korea.

Patent Abstracts of Japan, English language abstract of JP 09-258803, 2 pages (listed on accompanying PTO/SB/08A as document FP1).

Patent Abstracts of Japan, English language abstract of JP 10-097582, 2 pages (listed on accompanying PTO/SB/08A as document FP2).

Korean Intellectual Patent Office, English language abstract of KR 2000-0063796, 2 pages (listed on accompanying PTO/SB08A as document FP3).

Korean Intellectual Patent Office, English language abstract of KR 2001-0109944, 2 pages (listed on accompanying PTO/SB/08A as document FP5).

Korean Intellectual Patent Office, English language abstract of KR 2002-0071546, 2 pages (listed on accompanying PTO/SB/08A as document FP6).

Korean Intellectual Patent Office, English language abstract of KR 2002-0089225, 2 pages (listed on accompanying PTO/SB/08A as document FP7).

Korean Intellectual Patent Office, English language abstract of KR 2003-0025507, 2 pages (listed on accompanying PTO/SB/08A as document FP8).

Korean Intellectual Patent Office, English language abstract of KR 2003-0000426, 2 pages (listed on accompanying PTO/SB08A as document FP9).

Korean Intellectual Patent Office, English language abstract of KR 2003-0009755, 3 pages (listed on accompanying PTO/SB08A as document FP10).

Patent Abstracts of Japan, English language abstract of JP 2003-67485, 2 pages (listed on accompanying PTO/SB/08A as document FP11).

Co-pending U.S. Appl. No. 10/560,409, inventor Kim, S.-G., filed Jun. 14, 2004 (Not Published).

Co-pending U.S. Appl. No. 10/564,561, inventor Kim, S.-G., with a §371 date of Nov. 30, 2006 (Not Published).

* cited by examiner

FIG. 2a

| Int. code | Internal term name | Snomed cd | Snomed name | Snomed group | Int. class |
|---|---|---|---|---|---|
| 73190 | muscle disease | 75047002 | Disorder of skeletal muscle (disorder) | D1-50008 | Diagnosis name |
| 73191 | channelopathy | 106174000 | Function AND/OR dysfunction of axon (observable entity) | F-A80F9 | Diagnosis name |
| 73192 | myotonia | 3434004 | Myotonia (finding) | F-11430 | Dia. name |
| 73193 | myotonia atrophica | 193237003 | Myotonic disorder (disorder) | D1-5000C | Dia. name |
| 73194 | myotonia congenita | 57938005 | Congenital myotonia, autosomal dominant form (disorder) | DA-51322 | Diagnosis name |
| 73195 | Generalized myotonia(Becker) | 20305008 | Congenital myotonia, autosomal recessive form (disorder) | DA-51324 | Diagnosis name |
| 73196 | Myotonia levior(DeJong) | 8960007 | Myotonia levior (disorder) | DA-51344 | Diagnosis name |
| 73197 | Myotonia fluctuans | 193237003 | Myotonic disorder (disorder) | D1-5000C | 진단명 |
| 73198 | Myotonia permanens | 193237003 | Myotonic disorder (disorder) | D1-5000C | 진단명 |
| 73199 | Acetazolamide-responsive myotonia | 3434004 | Myotonia (finding) | F-11430 | Diagnosis name |

FIG. 2b

| Selected care phenomenon axis | Selected concept or attribute |
|---|---|
| Focus of care phenomenon | Pain |
| Decision | Sever(very high degree) |
| Frequency | Intermittent |
| Range | Left |
| Human body part | Leg |

Care diagnosis : severe(very high degree of) pain
Intermittent severe(very high degree of) pain
Intermittent severe(very high degree of) pain in leg
Intermittent severe(very high degree of) pain in left leg

FIG. 2c

| Selected care phenomenon axis | Selected concept or attribute |
|---|---|
| Focus of care phenomenon | Treatment provider role |
| Decision | Ineffective(low degree) |
| Likelihood | Very high likelihood |
| Bearer | Family |

Care diagnosis : ineffective(low degree of) treatment provider role
Very high likelihood of ineffective(low degree of)treatment provider role
Very high likelihood of family's ineffective(low degree of) treatment provider role

FIG. 2d

| Selected care action axis | Selected concept or attribute |
|---|---|
| Type of care action | Mitigation |
| Object | Pain |
| Beneficiary | Individual(patient) |
| Means | Cold water pack |
| Care arbitration : mitigate patient pain with cold water pack ||

FIG. 2e

| Selected care action axis | Selected concept or attribute |
|---|---|
| Type of care action | Education |
| Object | Treatment provider role |
| Beneficiary | Family |
| Means | Education material |
| Care arbitration : Family's treatment provider role education using education material ||

FIG. 2f

| Selected care phenomenon axis | Selected concept or attribute |
|---|---|
| Focus of care phenomenon | Pain |
| Decision | Severe(very low degree) |
| Frequency | Intermittent |
| Range | Left |
| Human body part | Leg |

Care diagnosis : severe(very low degree of) pain
Intermittent severe(very low degree of) pain
Intermittent severe(very low degree of) pain in leg
Intermittent severe(very low degree of) pain in left leg

FIG. 2g

| Selected care phenomenon axis | Selected concept or attribute |
|---|---|
| Focus of care phenomenon | Treatment provider role |
| Decision | Effective |
| Likelihood | Very high likelihood |
| Bearer | Family |
| Care diagnosis : effective(low degree of) treatment provider role<br>Very high likelihood of effective treatment provider role<br>Very high likelihood of family's effective treatment provider role | |

METHOD FOR COMPUTERISING AND STANDARDIZING MEDICAL INFORMATION

TECHNICAL FIELD

The present invention relates to a method capable of computerizing a variety of medical information, such as treatment information, nursing information and medicine information required in medical institutions, and standardizing the information.

BACKGROUND ART

As various kinds of networks such as the Internet as a worldwide network, LANs and the Intranet have advanced, there have been developed techniques and contents for enabling a variety of information to be shared over these networks.

Such technical advancement has also occurred in the medical industry, and techniques for sharing a variety of information over an internal network are being developed.

However, information sharing currently available within a hospital only allows the sharing of simple contents, such as personnel matters of users, treatment items, treatment reservation information, treatment particulars information and hospitalization information. In addition, only orders that doctors issue to patients after treatment, for example, information on whether to prepare which and how much medicine, whether to inject what injection, and whether to perform what examination, are being currently shared over these networks.

However, the most important information in the treatment and care of patients in a hospital is not the above listed information but individual status information depending on the disease symptoms of respective patients, such as nursing diaries written by nurses who observe the disease symptoms of patients, treatment opinions and treatment methods of doctors, and test and treatment results.

Meanwhile, the aforementioned information may be provided through charts written by doctors upon treating a patient, nursing diaries written by nurses upon caring for a patient, or various reports written by laboratory staff upon the testing or treatment of a patient.

However, there is a problem in that since there are a variety of contents to be input for respective clinical departments as well as a variety of means of acquisition for the aforementioned individual status information depending on the disease symptoms of the respective patients, such information cannot be indiscriminately standardized and computerized. Thus, there are currently no methods capable of sharing the aforementioned information over a hospital network.

In other words, there is a problem in that patient information cannot be managed more efficiently since the aforementioned individual status information depending on the patient's disease symptom are written in and managed through paper charts, even though network and computer techniques are being developed, and contents written in the paper charts are merely computerized by separate staff or systems.

There is a problem in that since the aforementioned information is not computerized, more rapid and accurate medical services cannot be provided to patients as patients are being examined or treated.

Meanwhile, the greatest contributor to problems in medical information is the fact that such information is not standardized. That is, insufficient standardization for medical information can be noted as one of the greatest problems in the development and settlement of such electronic records.

The need for medical information standardization as noted above will be described.

First, delays in the standardization of medical information are caused by the complexity of medical information itself as compared with information in other fields. That is, it is because medical information includes a variety of information formats such as text, images, photographs, and the like as well as simple numerical information, and the degree of processing of medical information varies from one-dimensional original information to completely processed high-dimensional information. Second, delays are caused by the fact that, in the medical industry, investment in information techniques is considered as "additional costs" unlike other fields. Third, delays are caused because the standardization task requires changes in medical practices.

Next, problems caused by non-standardization for medical information are as follows: First, such non-standardization obstructs the accurate and rapid collection of patient information. Second, it obstructs a user's access to patient information regardless of the place and system used. Third, it delays the development of a decision-determination system. Fourth, it delays clinical research and advancement using electronic medical records. Fifth, it obstructs medical treatment development through remote medical examination and education. Sixth, it obstructs the exchange of patient information and medical information. Finally, it delays research on quality evaluation, efficiency evaluation and management of medical treatment.

DISCLOSURE OF INVENTION

The present invention is conceived to solve the aforementioned problems. An object of the present invention is to provide a method for computerizing and standardizing medical information, which can provide web screens through terminals to enable doctors, nurses, pharmacists, or the like to immediately online input and read a variety of information created upon treating and caring for patients in a hospital, and can standardize medical information input or represented through the web screens, such as various medical information, nursing information, medicine information and the like.

BRIEF DESCRIPTION OF DRAWINGS

FIG. 2a is a diagram illustrating an embodiment of a SNOMED mapping table applied to the present invention.

FIGS. 2b to 2g are diagrams illustrating various examples of a method for stating a nursing statement sentence with standard terms.

BEST MODE FOR CARRYING OUT THE INVENTION

Figure 1:
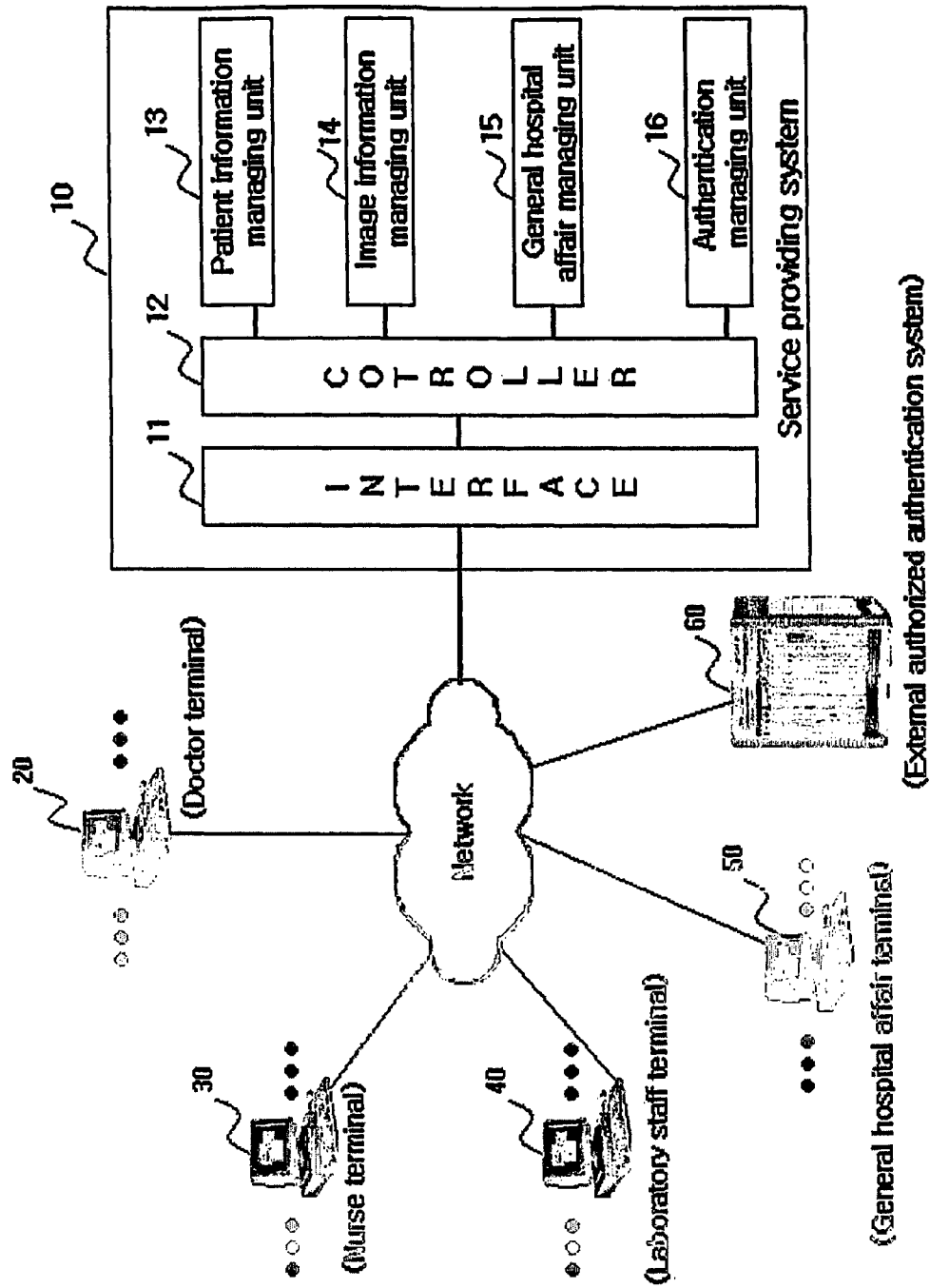
FIG. 1 is a diagram illustrating the configuration of an embodiment of a medical information-providing system to which the present invention is applied.

The meaning of the present invention will be described briefly prior to describing the present invention in detail.

Although diagnosis and examination methods in a modern medical science continue to develop, a doctor originally discriminates the disorder of a patient and determines the required action by listening to the patient's history. A chief complaint (hereinafter, referred to as cardinal symptom) is a first case history that a patient states and is a primary reason why the patient desires a medical service. The chief complaint is represented similarly to terms used by the patient. Therefore, the chief complaint is the first case history that a doctor meets, and the medical examination begins with the chief complaint.

Meanwhile, since electronic medical records (EMR) have been specified as a primary information technique in the medical treatment field by the U.S. Institute of Medicine (IOM, 1997) in 1991, effects of electronic medical records have been reported from several researchers. Electronic medical records result in improved medical information access, and high readability and completeness, and facilitating information inquiries by users due to the improved information inquiry and information integration. A decision-determining system capable of reducing medical examination errors in medical examination spots can be effectively applied through such electronic medical records, improved quality of medical treatment and medical standardization can be achieved through application of such medical guidelines or critical pathway, and the analysis of medical information and recreation of medical knowledge are facilitated through data warehousing.

However, such effects of electronic medical records cannot be easily obtained. That is, in order to obtain such effects, a need exists for the integration of well-configured systems, and particularly, a need exists for electronic medical records to which structuralized information and standardized medical terms are applied. The chief complaint is critical medical information needed for a decision-determining system, medical guidelines, critical pathways, and data warehouses, but the chief complaint in an existing medical record or the electronic medical record simply tends to be input in text form.

A variety of medical terms capable of representing medical concepts have been studied, but there are a number of obstacles in developing medical terms that can comprehend all such concepts. Particularly, at present, it is more difficult to implement a method in which terms represented by a patient are used with a defined representation principle in an actual medical examination environment. Currently, since one medical term system cannot represent all medical concepts, all areas of electronic medical records cannot be standardized as one medical term. Therefore, it is effective to provide a method in which suitable medical terms are applied to respective areas of electronic medical records and effective mapping between terms is defined. The U.S. information institute has proposed a standard term system corresponding to each area of medical science such as medicine, diagnosis, symptoms and signs, treatment, anatomic structure, or the like. A study has been reported as to whether a standard term system can correctly represent the meanings of terms used in clinical situations. However, if terms such as SNOMED, ICD-9-CM, UMLS and the like suggested by these studies are included on a listing of standardized chief complaints, such a list would be too vast to directly retrieve and use at a clinic, and requires a user to understand such standard terms. Consequently, there are difficulties in substantially using the terms.

Further, a number of medical term systems are not configured for the purpose of direct application in an actual clinical environment but are developed for the purpose of defining a reference terminology or concept relationships between terms. Therefore, in order to develop a chief complaint domain suitable for use in an actual clinical environment, it is required to extract or modify a set of proper terms from an existing standard term system, or to properly arrange and normalize chief complaint terms that have been used in existing medical records and map the terms to a medical term system suitable for the chief complaint term standardization. Since the chief complaint is composed of a variety of featured terms such as examination results, diagnosis names, treatment names and the like, as well as symptoms and signs, the standard medical term system is preferably a system capable of comprehending these contents.

Meanwhile, the Systematized Nomenclature of Medicine (SNOMED) studied and advanced by the U.S. College of American Pathologists is a proper term that can be applied to a group of chief complaint terms in an actual clinical environment.

According to the present invention, in order to build a chief complaint term system suitable for a hospital environment and familiar by users, a group of chief complaint terms applicable to hospital electronic medical records is formulated by arranging chief complaints used for existing medical records and extracting main concepts. Further, the present invention is intended to use this group of terms as material to build future Ontology-based Medical Vocabulary by mapping the group to SNOMED-CT terms, which is the standard term system.

FIG. 1 is a diagram illustrating the configuration of an embodiment of a medical information-providing system to which the present invention is applied.

As shown in the figure, the medical information-providing system to which the present invention is applied comprises a service-providing system 10 for managing and providing information on patients and managing general task information of a hospital through a network; a doctor terminal 20 for allowing doctors to connect to the service-providing system, read a variety of information on patients, and input treatment results; a nurse terminal 30 for allowing nurses to connect to the service-providing system, read the information on patients, or input treatment results; an laboratory staff terminal 40 for allowing various laboratory staff in the hospital to connect to the service-providing system, read information on a request for examination of patients, and input examination results into the service-providing system; a general hospital affair terminal 50 for allowing general staff responsible for general tasks in the hospital to connect to the service-providing system, and read or input a variety of information related to the hospital tasks; and an external authorized authentication system 60 for performing user authentication when the terminals are intended to be connected to the service-providing system.

At this time, a treatment task by a doctor, a nursing task by a nurse, and an examination task by a laboratory staff may be regarded as being performed on web screens of the doctor terminal 20, the nurse terminal 30 and the laboratory staff terminal 40, respectively. For the sake of convenience of illustration, the web screens executed by the respective terminals are called a doctor web screen, a nurse web screen and a laboratory web screen, respectively.

Hereinafter, the present invention will be described on the assumption that the service-providing system 10, the doctor terminal 20, nurse terminal 30 and the laboratory staff terminal 40 are connected over an internal network (Intranet) built into the hospital (hereinafter, briefly referred to as "Intranet"). However, the present invention is not limited thereto and the terminals may be connected and operated over a network such as the Internet.

Now, the Intranet will be described briefly below.

The Intranet refers to a group of networks, which are permanently connected to one another to create a more extended network, or a single network in a computing environment. The Intranet is a slightly different concept from that of a LAN (or WAN) owned by one group or the Internet that is a public network. That is, the Intranet uses TCP/IP for communication as well as using Internet techniques unlike a LAN. There is a difference between the Internet and an Intranet in that the Internet is a public network while an Intranet is a private network capable of blocking an intruder with a firewall.

Further, an Intranet may be much more complex than the Internet in that the Intranet is required to seamlessly interconnect several local networks which use different protocols and on which intelligent business applications are executed. Meanwhile, a user who has connected to an Intranet is allowed to connect to the Internet while connections from the Internet to the Intranet are limited, wherein only controlled access is permitted.

Further, as described above, an Intranet is different from a typical LAN in that the Intranet uses an Internet standard. Accordingly, in the case where a doctor, a nurse, an laboratory staff, or the like desires to connect to the service-providing system 10 using his/her terminal, he/she will connect to the system by driving a web browser as in an Internet connection method.

Further, according to the present invention, since a method for receiving various data from the service-providing system using the Internet based web browser as described above is used, storage mediums inside the doctor terminal 20, the nurse terminal 30, and the laboratory staff terminal 40 need not have any program and data for driving an application according to the present invention.

Further, although the general hospital affair terminal 50 and the service-providing system may be connected to each other by the Internet or an Intranet as described above, the present invention will be described by assuming that the general hospital affair terminal 50 and service-providing system are connected to each other by a general internal network such as LAN. At this time, if they are connected to each other by the general internal network as described above, software for receiving various provided information according to the present invention must be installed in the general hospital affair terminal 50.

Meanwhile, in order to provide service according to the present invention, the service-providing system 10 includes an interface 11, a control unit 12, a patient information-managing unit 13, an image information-managing unit 14, a general hospital affair managing unit 15, and an authentication-managing unit 16.

First, the interface 11 performs a function of connecting with the respective terminals 20, 30, 40 and 50, and the external authorized authentication system 60 via the network. That is, the interface 11 performs a connection via the Intranet with the doctor terminal 20, the nurse terminal 30 and the laboratory staff terminal 40, while performs a function to allow Internet connection if there is an Internet connection request from the terminals. Further, the interface 11 may be connected with the general hospital affair terminal 50 over the internal network such as the LAN. Further, as described above, the interface may be connected with the external authorized authentication system 60 over the Internet.

Next, the patient information-managing unit 13 performs a function of managing patient information (medical information) input from at least one of the doctor terminal 20, the nurse terminal 30, the laboratory staff terminal 40, and the general hospital affair terminal 50, and of extracting and transmitting medical information on a relevant patient if there is an information request for the relevant patient from the doctor terminal 20.

At this time, medical information for implementing the method for computerizing and standardizing medical information according to the present invention may be managed by a separate system or a managing unit or may be managed by the patient information managing unit 13 in an integrated manner, wherein the medical information includes various standardized diagnosis names (disease names), operation names, cardinal symptoms, nursing statement sentences (sentences that can be used by nurses to represent the status of the patient), medicine names, doctor statement sentences (sentences that can be used by doctors upon patient medical examination to represent the status of the patient), various mapping tables, and various standardized code (SNOMED CODE, ICNP CODE, ATC CODE, etc.) information used in medical field.

That is, the present invention is intended to standardize a variety of information systematically and transmit the information to a web screen of each terminal, and also to standardize and manage information transmitted from each web screen.

Next, the image information-managing unit 14 performs a function of managing image information input from at least one of the above respective terminals, and of extracting and transmitting image information on a relevant patient if there is an image information request for the relevant patient from the doctor terminal 20. Typically, the image information refers to images obtained by electronically imaging various photographs or the like photographed to examine patient states, such as X ray photographs, endoscope photographs, CT photographs, and the like. The image information includes images obtained by scanning various documents, photographs, or the like as well as the aforementioned photographs.

Next, the general hospital affair managing unit 15 performs a function of managing hospital affair related information input through the general hospital affair terminal 50 by staff responsible for general management tasks of the hospital, and of transmitting hospital affair related information to the relevant terminal if there is a request to output the information from at least one of the general hospital affair terminal 50 and other terminals 20, 30 and 40.

Next, the authentication-managing unit 16 performs a function of performing authentication on respective users that enter the service-providing system 10 over the network (e.g., Internet or Intranet). That is, if a doctor, a nurse, laboratory staff, and a general hospital task staff desire to connect to the service-providing system 10 using their terminal, the authentication-managing unit 16 performs a function of permitting a connection only to authenticated users by performing an authentication procedure to confirm whether they are users authorized to access. Meanwhile, for a system that manages patient information in a hospital like the service-providing system, it needs thorough security, wherein sufficient security may not be provided only by self-authentication. Accordingly, in this case, an authentication procedure may be performed by the external authorized authentication system 60 other than the internal authentication system connected to the Intranet. That is, if there is an authentication request from a user, the authentication-managing unit 16 transmits the user information to the external authorized authentication system 60 over a network such as the Internet to perform the authentication procedure, and then determines whether to allow connection based upon the authentication result.

Finally, the control unit 12 performs the function of controlling the interface and respective units 13 to 16, and transmitting or receiving a variety of information to or from the terminals over the network.

At this time, the interface and the respective units 12 to 16 may be implemented by one computer or server, and include a secondary system used as a backup in case of failure.

Meanwhile, according to the present invention, the standardization of a variety of medical information can be greatly classified into three meanings.

First, it means that terms used with a variety of names by the respective doctors or nurses, for example, terms that can be standardized (hereinafter, referred briefly to "standard terms") with respect to terms regarding cardinal symptoms for patients, diagnosis names, operation names, terms used by nurses upon writing the status of the patients, terms used by doctors upon writing the status of the patients, prescription terms ad medicine terms used by doctors, and the like. Meanwhile, hereinafter, concepts of the respective standard terms will be described with concepts being greatly divided into doctor related standard terms and nurse related standard terms. That is, doctor related standard terms may include terms regarding cardinal symptoms of patients (hereinafter, referred briefly to as "cardinal symptoms"), diagnosis names, operation names, terms used by doctors upon writing the status of the patients (doctor statement sentences), prescription terms and medicine terms, and the like used by the doctors, and the nurse related standard terms may be classified into terms used by nurses upon writing the status of the patients (hereinafter, briefly "nursing statement sentences").

Second, it means that if international standard terms or standard codes (hereinafter, referred briefly to as "standard codes") are already present in the above-selected standard terms, the above-selected standard terms are mapped to the standard codes. At this time, the codes are not necessarily international standard codes. Alternatively, if there are no standard codes, self standard codes may be formulated and mapped.

Third, it means that the above-selected various standard terms are systematically provided through the web screen executed on each of the terminals.

Hereinafter, the first and second processes (processes of building a database) will be first described with reference to FIGS. 2a to 2g. Then, the third processes (processes of using and managing the database) will be described with reference to FIGS. 3a to 3e and FIGS. 4a to 4h.

FIG. 2a is a diagram illustrating an embodiment of a SNOMED mapping table applied to the present invention, and FIGS. 2b to 2g are diagrams illustrating various examples of a method for stating a nursing statement sentence with standard terms.

First, various medical treatment standard codes applied to the present invention will be described briefly prior to describing a process in which a variety of terms in the medical industry are built into a database by standard terms and a process in which various standard codes are mapped to the standard terms.

Currently, there are various types of standard codes used as international standards in the medical industry. Hereinafter, descriptions of classified doctor related standard codes and nurse related standard codes will be given.

First, doctor related standard codes will be described.

First, there is International Classification of Disease (ICD) (hereinafter, briefly referred to as "ICD"). The ICD was first defined in 1893 and then gradually revised up to ICD-10 in 1992. This classification classifies diagnosis names having common features, for example, dyscrasia having common etiology or of common organs using a core classification. Each of the classifications is further classified three sub-classifications to denote each diagnosis name, and is configured of 4 to 5 digits. The ICD-9 revised in 1977 was classified according to etiology, anatomic structure, and detailed form, and has a core classification of 3 digits. A fourth digit is added as a decimal digit. For the fourth digit, the numbers 0 to 7 mean more detailed disease classification in the core classification, 8 means "other", and 9 means "non-specified." In addition to the diagnosis names, it includes classifications regarding medical-specialty diagnosis, health-status, disablement, procedure, and reasons for contact with healthcare provider (symptoms). However, ICD-9 is insufficient as a code for medical statistics in the U.S. and accordingly has classified in more detail. That is, ICD-9 CM (clinical modification) having additional fourth and fifth digits has been announced and used. This is currently used as a basic code for health insurance payment or the like in U.S. The ICD-10 was defined in 1992 and was intended to add and modify the insufficient ICD-9, and is represented by an English capital letter and two to three digits. Further, a code to solve a problem was newly added. Recently, the ICD-10-PCS (procedure coding system) regarding ICD-10CM, medical treatment and the like was announced.

Second, the Unified Medical Language System (hereinafter, briefly referred to as "UMLS") was developed in 1989 to effectively collect and store medical information on a variety of information source and a variety of systems and to provide the stored information. The largest obstacle in collecting and storing a variety of medical information is that the respective systems use different term systems and that the source of the medical information varies greatly. This fact acts as an obstacle both to medical related workers and medical system developers. The UMLS knowledge system is roughly constructed of three main portions. That is, it is constructed of Metathesaurus, Semantic network, and Specialist Lexicon of concepts. Additionally, an Information source Map has recently been added. The Metathesaurus provides central term elements of the UMLS, and provides definitions of terms, classification systems, and relationships with relevant terms in each term system, and the like. The Metathesaurus has 800,000 concepts and 1900,000 terms obtained by incorporating 60 terms and classification systems.

Third, SNOMED has been studied, developed and used over a period of 35 years or more. At this time, a code for a term is composed by mixture of codes corresponding to the respective module. For example, the code is mixed in the following form:

T+M+E+F+D lung granuloma *M. tuberculosis* Fever Tuberculosis T-2800 M-44060 E-2001-07-29 F-03003 D-0188

That is, the status of patients may be represented by combining respective SNOMED codes.

The aforementioned SNOMED code will be described in more detail.

That is, SNOMED CT is a standard medical term system made by combining the existing SNOMED RT and Clinical Term Version 3 (Read codes) with cooperation of the College of American Pathologists and the British National Health Service. A second edition was released in January 2003. The SNOMED is a term system based on medical concepts and satisfies conditions medical terms must have. The SNOMED has 14 top hierarchies wherein one top hierarchy includes a variety of granularities. One concept belongs to one top hierarchy, and has one concept code (concept identifier) and several descriptions. The respective concepts have a parent-child relationship and a number of other relationships, and are discriminated and classified through multiple hierarchies. Term concepts, descriptions, and relationships are core files constituting the SNOMED CT, each having concept identifier, description identifier, and relationship identifier and being associated with each other for the concept identifier. The SNOMED CT provides medical classifications of ICD-9-CM, ICD-O and ICD-10 (British version), NIC and NANDA as nursing terminologies, and association information; and American English, British English, and Spanish versions of SNOMED CT are currently available.

The core hierarchy of the SNOMED code will be described. As of 2003, 344,549 unique concepts are contained in the concept table, and 913,696 descriptions are contained in the descriptions table. The respective concepts are interconnected by a variety of relationships including a parent-child relationship (IsA relationships), and a total of 1,324,152 relationships are contained in the relationship table. The respective concepts have status information (Concept Status, Description Status, Relationship Status) as used, and are classified into currently used concepts (current), unused concepts (retired, duplicated, outdated, ambiguous, erroneous, inappropriate, non-current), definition-modified concepts (moved elsewhere), and range-limited concepts (limited).

Other structures of the SNOMED code will now be described. SNOMED CT provides a specific area or institutes with a subset mechanism capable of discriminating unique term concepts, and also provides a cross-mapping mechanism with LOINC, ICD-9-CM, ICD-O, and ICD-10. In addition, SNOMED CT manages each concept and a version of a table structure (History mechanism) and also provides a developer toolkit to term developments together so that the SNOMED can be applied to each institute.

An additional retrieving toolkit related to the SNOMED code includes a CIC look up engine (CLUE) browser, and the CLUE retrieving screen is a retrieving toolkit that is provided to users using the SNOMED CT, which is manufactured by British Clinical Information Consultancy (CIC) and is distributed by U.S. College of American Pathologists. It is possible to easily recognize term concepts, relationships, descriptions, and structures that the concepts belong to, through the CLUE retrieving screen.

Meanwhile, standard codes such as Medical Subject Headings (MeSH) and Read Clinical Codes are being used in addition to the aforementioned standard codes.

At this time, although standardization can be made using at least one of the respective codes, medical information such as various cardinal symptoms, diagnosis names, and operation names is preferably mapped to the SNOMED CODE in view of the properties of each standard code. This is because the SNOMED code among the aforementioned codes can represent clinical concepts most abundantly.

Next, nurse related standard codes will be described.

That is, the international standard codes particularly related to medical examination actions by doctors in the medical industry have been described so far and hereinafter international standards particularly related to care actions by a nurse in the medical industry will be described.

There is the International Classification for Nursing Practice (ICNP) (hereinafter, referred briefly to as "ICNP") as an international standard related to care actions.

The ICNP was developed by the International Council of Nurses (hereinafter, referred briefly to as "ICN") in 1999 with the purpose of providing a nursing terminology integrated system capable of describing nursing practice. That is, the ICNP is a standard code capable of describing various care related information that covers care phenomenon (problems), care actions (arbitration), and care results (responses).

At this time, as the SNOMED code is used for describing medical information related to a medical examination action by doctors, the ICNP code may be used for describing a variety of medical information related to care actions. Further, the aforementioned other codes may be used in addition to the SNOMED code and ICNP code. The SNOMED code may be used even in describing medical information related to various care actions by a nurse, and vice versa.

Hereinafter, a method for building standard terms into a database and a method for mapping the standard terms to the aforementioned various standard codes for the purpose of the method for computerizing and standardizing medical information according to the present invention will be described.

At this time, a term standardizing range in the present invention can be greatly divided into doctor related standard terms and nurse related standard terms, as mentioned above. Particularly, cardinal symptoms, diagnosis names, and operation names among the doctor related standard terms will be described by way example while nursing statement sentences among the nurse related standard terms will be described by way of example. However, the present invention is not limited only to standard terms, and may be also applied to clinico-pathologic tests, treatment names and various free-texts in addition to doctor statement sentences, prescription terms used by doctors, and medicine terms.

First, term standardization for cardinal symptoms among a variety of medical information as described above may be made by analyzing admission charts built in the hospital over several years and performing question-investigations on users. Meanwhile, it is analyzed that the types of overall cardinal symptoms investigated in an example of a Seoul university hospital amount to 80,699 cases, in which cardinal symptoms input two times or more amount to 10,728 cases and cardinal symptoms input 100 times or more amount to 187 cases. That is, according to the present invention, the most generally used cardinal symptom terms are sorted through such an analysis and are applied to the medical information-providing system, and the cardinal symptom terms are mapped to the SNOMED code or the ICNP code, such that medical information can be smoothly shared among a number of domestic or international hospitals. That is, the medical information-providing system in each hospital uses standard terms such that confusion in term utilization is prevented, the standard term can be used in nationwide hospitals such that nationwide medical information is standardized, and further the standard terms are mapped to the international standard codes such that worldwide medical information is shared.

The meaning and process of term standardization for cardinal symptoms (called chief complaints) will be described in more detail.

First, chief complaints were extracted from a computerized discharge summary paper containing about 235,000 cases over the past seven years in the Seoul university hospital having about 300,000 admission cases in one year in order to arrange chief complaints. That is, 220,200 chief complaints which correspond to 93.5% of the chief complaints in the discharge summary paper containing 235,426 cases were input.

Next, the process of normalizing chief complaints will be described. That is, contents input into chief complaints are separated according to each meaning and then are aligned on a term spelling basis. Misspellings and abbreviations of chief complaints are restored to full spellings and ambiguous chief complaints were excluded. The chief complaints were divided into main concepts, concept qualifiers, and concept modifiers. The concept qualifier is a term or a clause that changes the main concept of a term in a temporary or managing aspect, and for example is defined as representing the past status (history of), the status of the main concept (status post, ruled out) and the like. The concept modifier is a term or clause that changes the meaning of the main concept in a clinical aspect, and is defined for example as representing the degree of the symptom (i.e., severe, moderate, and mild), disease (stage I), and the like. Selection of terms in main concepts is defined as a minimum concept unit that can be used in an actual clinic, and is selected by the name of a dedicated doctor in each department. For example, for pain among atomic concepts, the main concept term also includes abdominal pain, right upper quadrant pain, and the like so that they are effectively used in a clinic. Main concepts of classified chief complaints are again aligned on a spelling and concept basis, and then 6317 representative chief complaints are extracted into analysis targets.

Next, mapping the representative chief complaints to the aforementioned SNOMED CT will be described. That is, the present invention makes it a rule to mapping the representative chief complaints and the concepts of SNOMED CT, and also makes pre-coordinated mapping a rule. That is, the concept identifier is retrieved the concept table of SNOMED CT and is imparted to the representative chief complaints. If the representative chief complaint and the concept are not matched to each other, a concept similar to or broader than the chief complaint is retrieved from SNOMED CT and is mapped. At this time, the mapping task is performed with several principles. First, if the same spelling belongs to a variety of concepts, the most suitable concept for the character of the chief complaint among the concepts is selected. For example, a retrieved mass includes two concepts of a mass (morphologic abnormality; conceptid=4147007) and a mass (a measure of quantity of matter (property) (qualifier value); conceptid=118538004), and the mass (morphologic abnormality; conceptid=4147007) suitable for the chief complaint is selected. Second, if in SNOMED, they are the same in a parent-child relationship and other relationships and are classified into a number of concepts, and a difference between two concepts is ambiguous clinically, one term is taken and mapped consistently. For example, if retrieval is carried out by anorexia, loss of appetite (finding) and appetite loss-anorexia (finding) are retrieved beneath a parent structure of the finding of quantity of appetite, and a relationship between them has only the IsA relationship in common. In this case, the appetite loss-anorexia (finding) is taken. Third, if the meaning of the representative chief complaint is subdivided in SNOMED CT, a top concept capable of representing the comprehensive meaning of the chief complaint is taken. For example, if weight loss as a chief complaint is retrieved from SNOMED CT, two concepts of abnormal weight loss (finding) and excessive weight loss (finding) are retrieved beneath the concept of the weight loss finding (finding). If it is unclear whether the chief complaint of abnormal weight loss or excessive weight loss is a representative chief complaint, the weight loss finding (finding), which is a top concept of two concepts, is selected. Fourth, if chief complaints of the same concept and the same spelling have a duplicate concept status, the currently used current status is selected. For example, if nausea is retrieved, nausea (finding) having a current status and nausea NOS (finding) having a limited status could be found and in this case the nausea (finding) is selected. Fifth, overlapping or unclear concepts, such as NOS, not specified, unspecified and the like, among the concepts of SNOMED CT are not selected if possible.

Next, arrangement of mapped chief complaints will be described. The chief complaints that have been mapped to SNOMED CT are divided and arranged into the following classifications. First, the chief complaints are classified and arranged into a case where the representative chief complaint and the concept of the SNOMED CT are exactly matched, a case where the concept of the SNOMED CT is broader than the concept of the representative chief complaint, a case where the concept of the representative chief complaint is broader than the concept of the SNOMED CT concept, a case where the representative chief complaint and the SNOMED CT concept are not matched or comprehensive and are overlapped in part, and a case where they are not matched to each other at all. Second, the mapped chief complaints are classified and compared according to the top hierarchy of SNOMED. Third, if mapping is not made by the pre-coordinated mapping method, it is carried out by a post-coordinated mapping method.

Next, application of a set of chief complaints will be described. That is, the set of arranged chief complaints is disclosed to users (medical persons) and responses from users are investigated for two divided portions. First, chief complaints expected to be frequently used by users are investigated to confirm where they are included in the set of chief complaints. Second, chief complaints to be added are investigated.

Further, in a case of the diagnosis names, diagnosis names required by the user are analyzed through analyzing a number of diagnosis names currently used or through various questions, and the diagnosis name having the highest frequency is selected and adopted as a standard term and then is mapped to an international standard code.

Further, in the case of operation names, among terms obtained by investigating diagnosis names of currently available operations, E DI codes for insurance requests, and operation names required by the users, some are adopted as standard terms in view of frequency, accuracy of terms, and the like, and are mapped to the International standard code.

Further, various medical information as mentioned above is adopted as standard terms by the above method and is mapped to the international standard code.

Meanwhile, as for a mapping method to the international standard code, one standard term is preferably mapped to one standard code in a one-to-one manner, and many-to-one, one-to-many, and many-to-many mappings are possible if necessary. That is, several standard terms may be mapped to one standard code and vice versa.

A mapping example of SNOMED CODE as described above is shown in FIG. 2a. That is, FIG. 2a illustrates an embodiment of a SNOMED mapping method that is applied to the present invention, and particularly illustrates an example in which various terms used in the diagnosis name is mapped to the SNOMED code.

As shown, the SNOMED mapping table applied to the present invention includes an internal code and an internal term name used in the service-providing system 10, and includes a SNOMED code, a SNOMED name, and SNOMED group mapped thereto. Further, the internal classification is classification used in the service-providing system 10 to which the present invention is applied, and classified and managed into a diagnosis name, a cardinal symptom, an operation name and the like.

That is, according to the present invention, it is possible to arrange and standardize terms that can be used as a standard among numerous medical terms used in a variety of forms by each hospital or doctor through a SNOMED mapping table as shown in FIG. 2a, and to computerize medical terms internationally as well as domestically by mapping the terms to the international SNOMED code. Meanwhile, the mapping tables shown in FIG. 2a is stored and managed in the service-providing system.

Next, it is possible to select such standard terms and map the standard terms to the standard code with respect to terms (nursing statement sentences) used upon writing the status of a patient by nurses. At this time, a term used by nurses may be further divided and managed into terms dependent on care phenomenon (problems), care actions (arbitration), and care results (responses).

At this time, care phenomenon may be reclassified and managed into nursing practice focus, judgment, frequency, time, topology, body site, likelihood, distribution, and the like.

That is, a nursing practice focus is an attention area described by social responsibility and is a professional conceptual frame of a professional nursing practice. For example, for a focus of pain, pride, and weakness, the family and regional societies are contents corresponding to non-distributed decisions, namely, a collective decision. Further, the judgment includes clinical opinions, deductions, or determination of professional nursing practices related to the care phenomenon, and quality or representation degree care phenomenon intensity. Further, the frequency includes concepts of generation or number of repetition times a care phenomenon appeared over a certain time, for example intermittent, frequently, and the like. Further, Time includes concepts such time length for which a care phenomenon continues. Further, the topology includes concepts such as an anatomic area related to the centerline of a human body or an anatomic range of care phenomenon, for example right, left, part, and whole. Further, body site includes a concept of an anatomic position where a care phenomenon appears, for example eyes, fingers and the like. Further, likelihood includes the probability or possibility to generate a care phenomenon, for example, concepts such as risk, chance, and the like. Further, distribution corresponds to an object as having a care phenomenon, the meaning of a bearer, and distributed determination, and includes concepts such as individual, family, local society and the like.

Meanwhile, care actions include detailed concepts, such as action type (actions performed by the care action, such as education, insertion, monitoring), target (objects affected from the care action or objects delivering the care action, such as pain, infant, and home service), and means (objects used to perform the care action. The means includes tools (a toolkit used for the care action), services (a specific task or plan used for the care action), such as bands, a bladder training technique, and a hospital discharge procedure), time (a time point (event) when a care action is provided and which is defined by divided instants), and time interval (episodes) which is defined as a time between two events. It includes upon discharge, under operation, before birthing, topology (an anatomic area related to the center line of a human body or an anatomic range of care phenomenon, such as right, left, portion, whole), body site/location (an anatomic position and a place position where the care action is performed. The body site means an anatomic site or position, and the locations means a special position where the care action is performed, such as head, arm, home, and company), a route (the route in which the care action is performed, such as oral cavity, hypoderm), and a beneficiary (an object obtaining benefits from performed care action, such as individual, and group.

Meanwhile, FIGS. 2b to 2g are diagrams illustrating various examples of the method for stating a nursing statement sentence with standard terms, and illustrate examples in which the aforementioned care phenomenon is stated by standard terms. That is, they illustrate an example in which one nursing statement sentence is formed by individually selecting terms classified in standard terms. That is, as shown, the nurse will be able to input one completed nursing statement sentence through the web screen by selecting and combining standard terms provided through the nurse web screen output on the nurse terminal 20. Further, since the respective input standard terms is mapped with the international standard code, if the relevant standard term is selected, patient information in which the standard term has been used will be able to be read. Further, using such a method, the doctor may input a doctor statement sentence on the doctor terminal 30.

That is, FIGS. 2b and 2c illustrate care phenomenon and care diagnosis, FIGS. 2d and 2e illustrate care actions and care arbitration, and FIG. 2f and 2g illustrates care phenomenon and care results.

Various medical information is built in a database by standard terms using the method as described above, is mapped to various international standard codes, and is managed through the patient information managing unit 13 or the separate managing unit.

Meanwhile, hereinafter a method for managing or u sing such standard terms through a web screen will be described with reference to FIGS. 3a to 3e and FIGS. 4a to 4h.

FIGS. 3a to 3e are diagrams illustrating various examples of a method for providing standard terms for a doctor through a doctor web screen in the method for computerizing and standardizing medical information according to the present invention; and FIG. 4a to 4h are diagrams illustrating various examples of a method for providing standard terms for a nurse through a nurse web screen in the method for computerizing and standardizing medical information according to the present invention.

That is, each of the aforementioned standard terms is provided in the form of a menu or checkable identity through a web screen of each of the doctor terminal 20, the nurse terminal 30, the examination room staff terminal 40, and the general medical affair terminal 50 so that it can be selected and used by a user. Further, managers of the web screen may perform various management activities such as newly registering, deleting and modifying standard terms through the web screen.

At this time, a method for representing the standard terms on the web screen is greatly classified into three methods.

A first method is a method in which the respective standard terms can be selected by one check item. For example, in the case where the doctor desires to input cardinal symptoms of patients on the doctor web screen, if a number of standard terms related to the cardinal symptoms are provided through the web screen, the doctor will select or check a desired cardinal symptom standard term among the number of standard terms related to the cardinal symptoms, wherein the selected or checked cardinal symptom standard term is stored as cardinal symptom information regarding the patient in the patient information managing unit 13.

A second method is a method in which is provided in the form of a statement sentence record other than such a simple selection or check matter. That is, when a nurse desires to formulate a statement sentence (nursing statement sentence) for the status of a patient generated upon caring for the patient, the nurse will select a relevant item for each item among the standard terms, wherein the control unit 12 will make one statement sentence by combining the selected items (See FIGS. 2b to 2g).

A third method is a method for managing such various standard terms through the web screens.

Hereinafter, a method in which the three methods are implemented through a web screen will be described with reference to the accompanying drawings.

First, a process of implementing the first and third methods through the doctor web screen will be described.

Figure 3A:
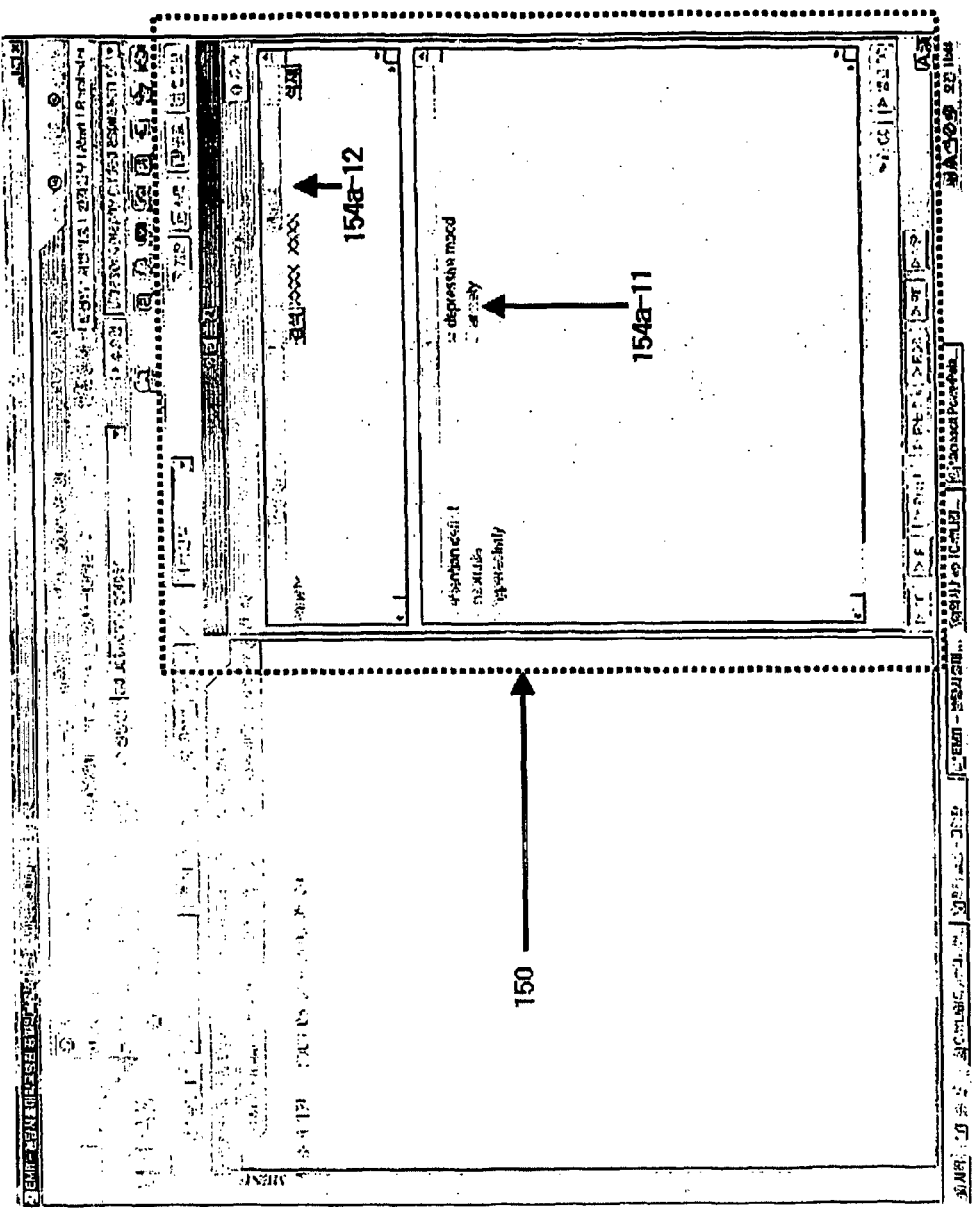
FIGS. 3a to 3e are diagrams illustrating various examples of a method for providing standard terms for a doctor through a doctor web screen in the method for computerizing and standardizing medical information according to the present invention.

That is, FIG. 3a illustrates a doctor web screen that can be output on the doctor terminal 20, and particularly illustrates a patient information input portion 150 on which a doctor can input cardinal symptom information regarding patients (an example in which the first method is applied). As shown, a variety of standard terms (154a-11) capable of representing cardinal symptoms for patients are output, wherein the doctor recognizes symptoms of a patient while examining the status of the patient and selects a cardinal symptom standard term related to the patient among the standard terms. At this time, the selected cardinal symptom standard term may be displayed on a separate window (154a-12). If the doctor discovers and stores all standard terms related to desired cardinal symptoms, the input cardinal symptom information is stored in the patient information managing unit 13. Thereafter, there is a request for the cardinal symptom from each web screen, the cardinal symptom information is transmitted and output to the relevant web screen.

Figure 3B:
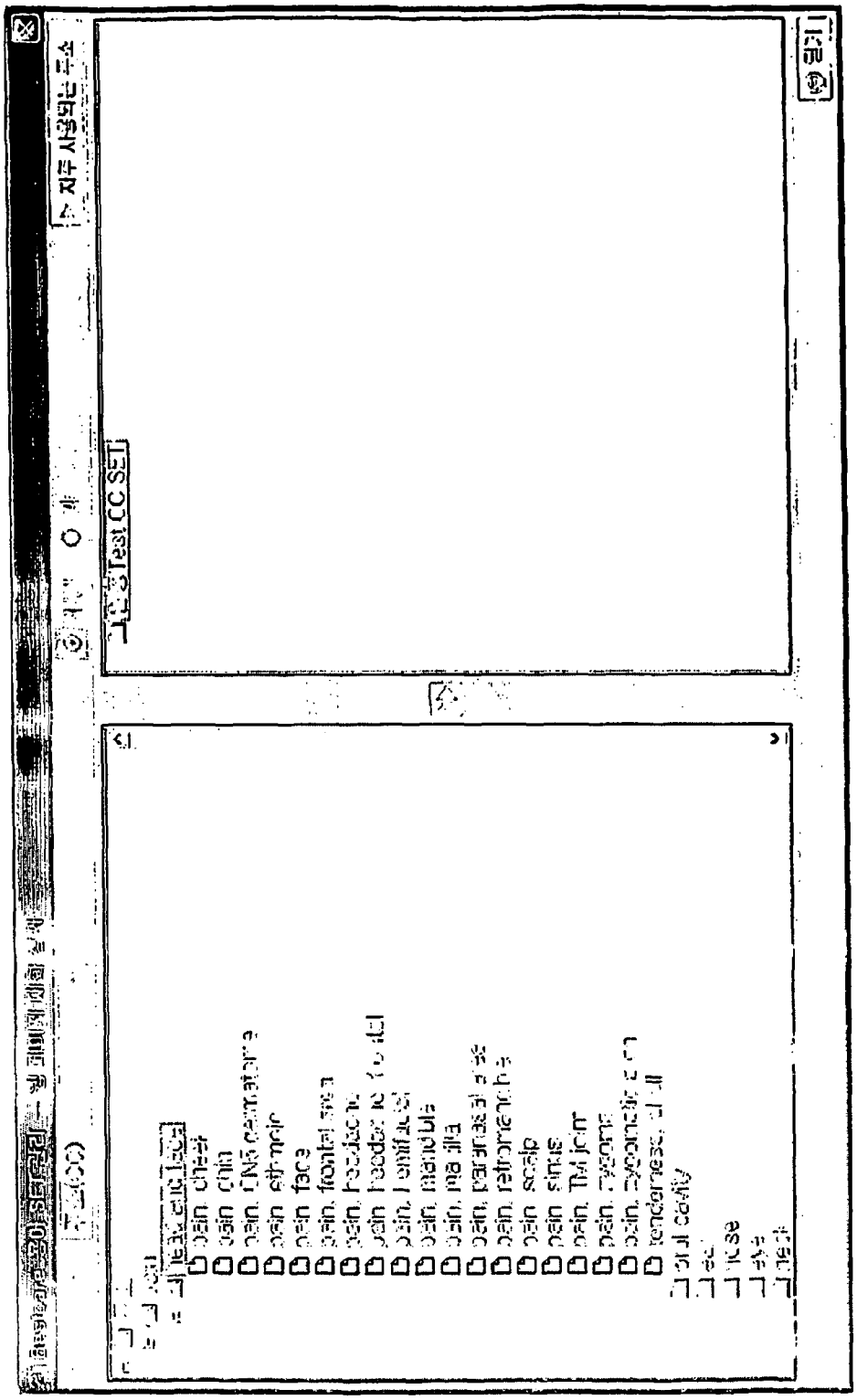
Figure 3C:
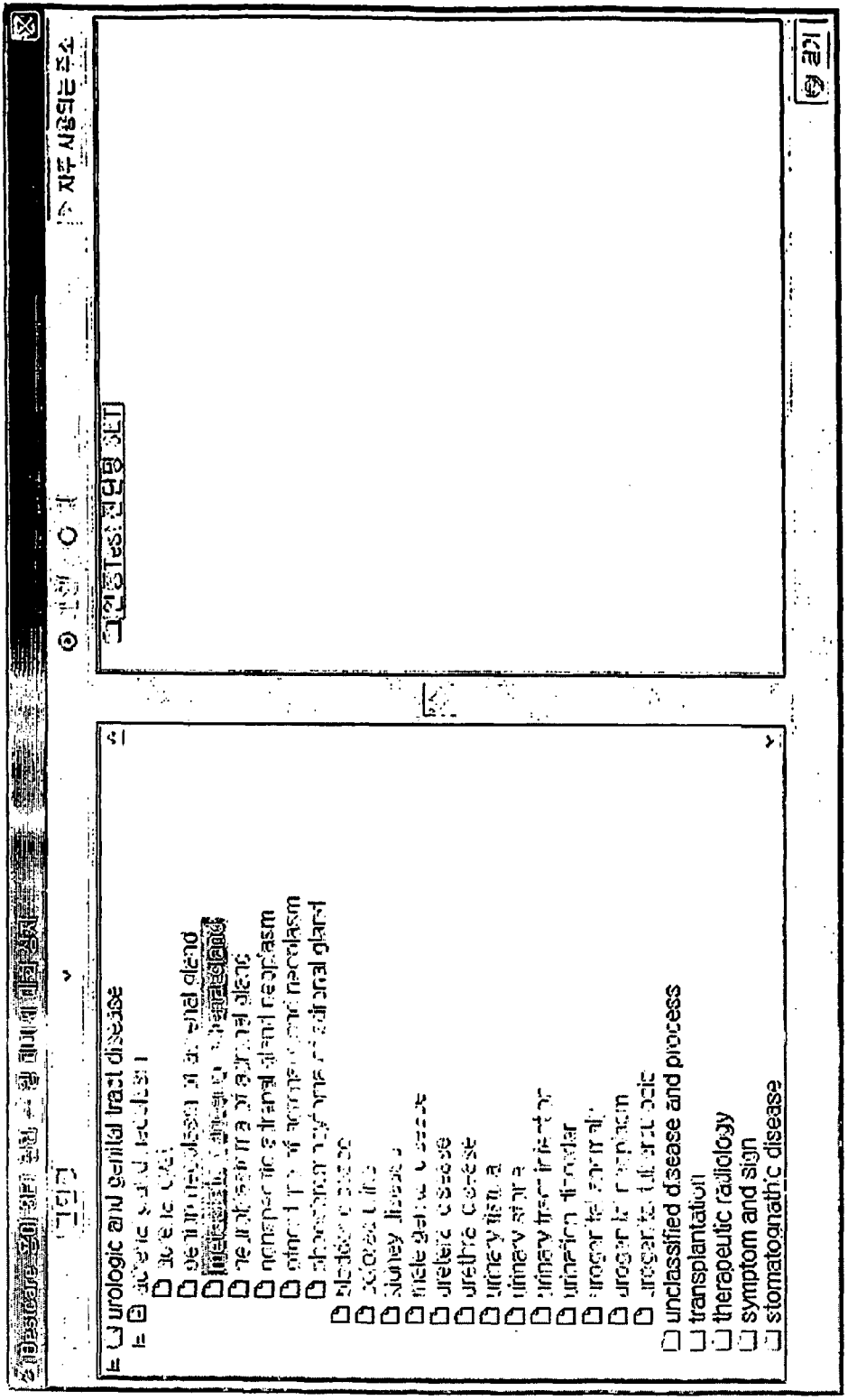
Figure 3D:
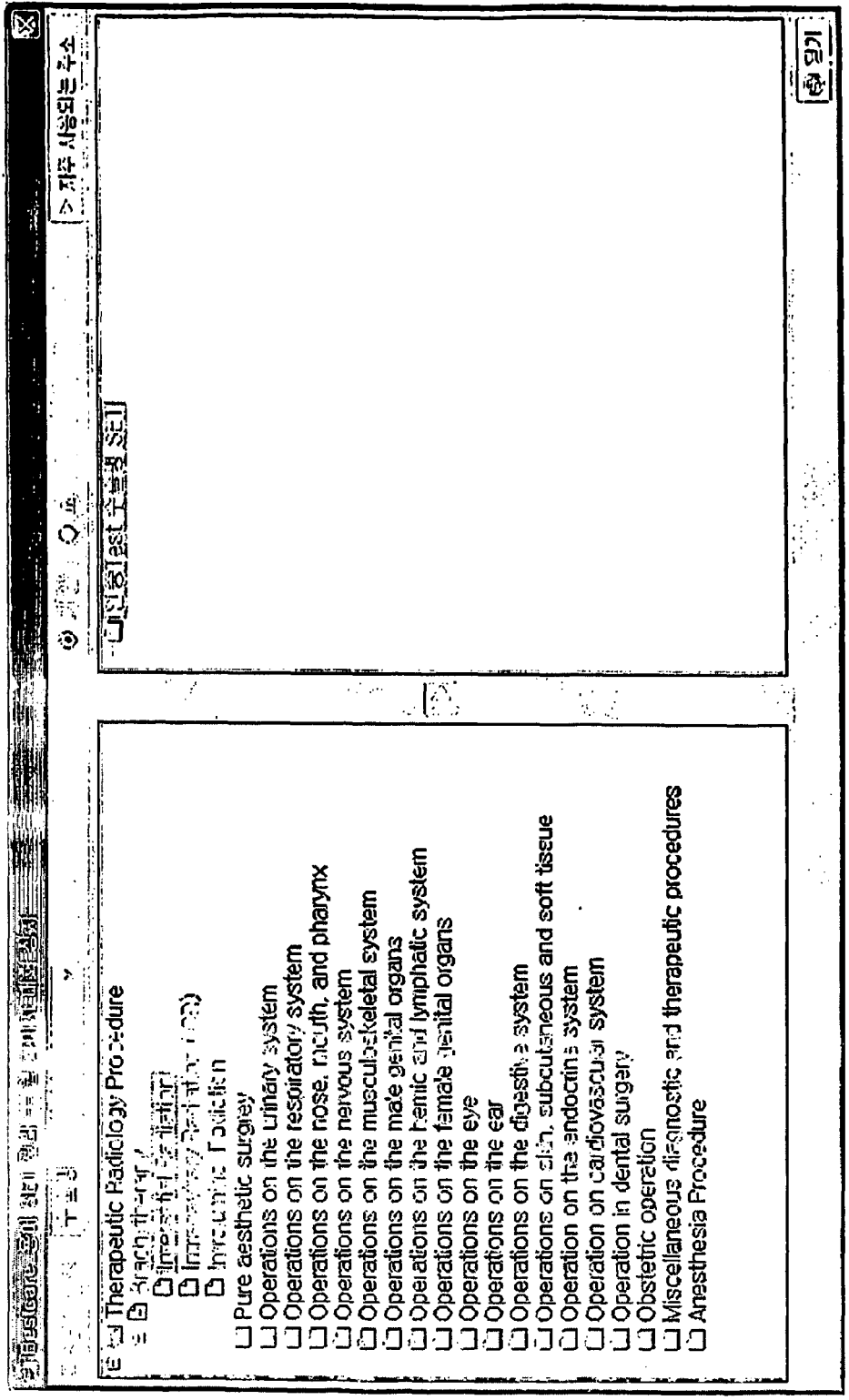
Figure 3E:
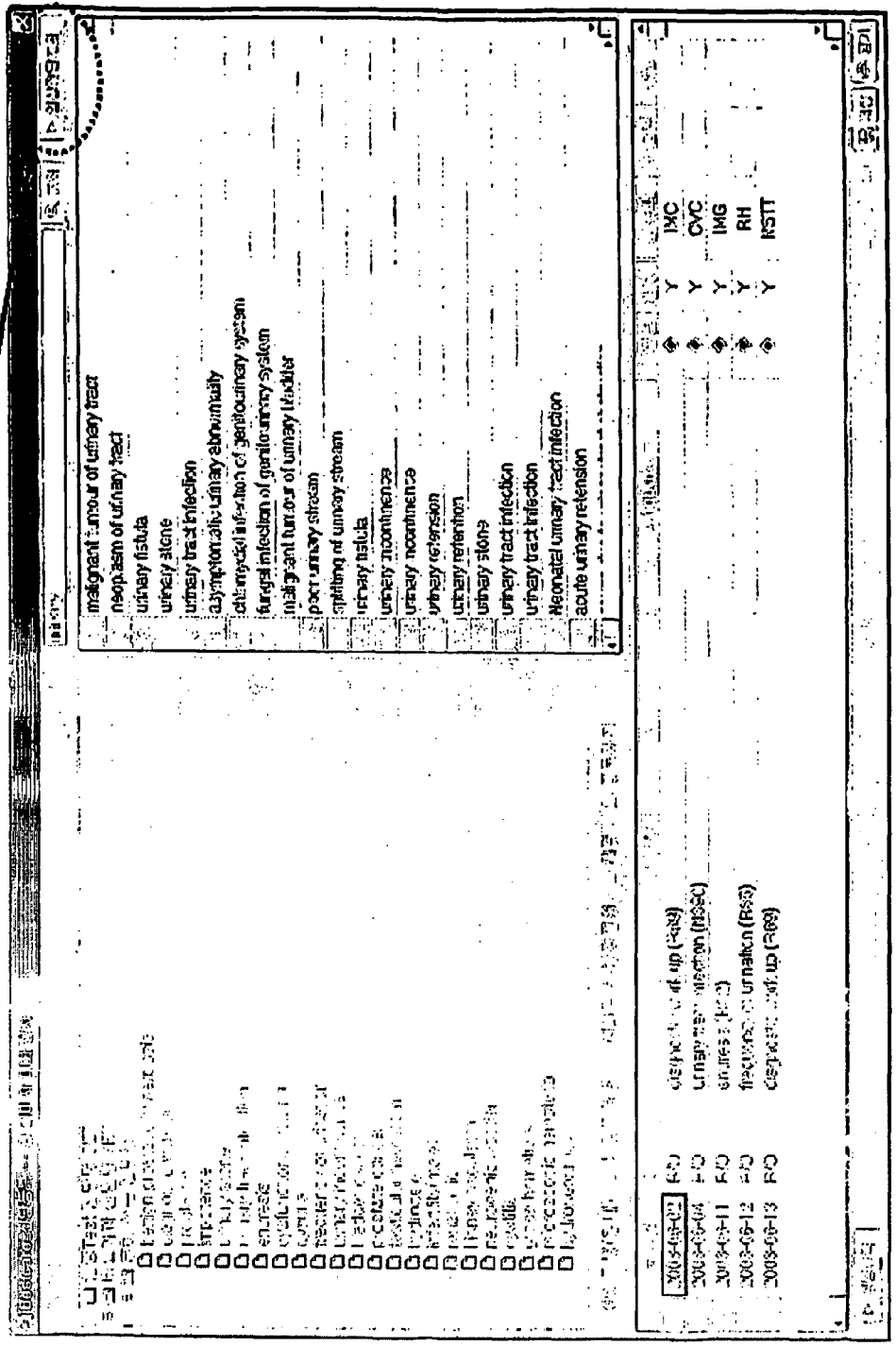

Further, FIGS. 3b to 3d illustrate an example in which the cardinal symptoms (chief complaints), diagnosis names and operation names among doctor related standard terms are provided through a dialog box of the doctor web screen, so that a set of terms frequently used by a doctor are managed and used for each individual or department (an example in which the second method is applied). That is, doctors will be able to arrange the doctor related standard terms through the dialog box as shown, and retrieve and use or register the standard terms through the dialog box. Particularly, FIG. 3e illustrates a screen on which a doctor can retrieve, select and register standardized diagnosis names upon examining patients.

At this time, the respective standard terms shown in FIGS. 3b to 3e are terms selected through the standardizing process as described above. The standard terms are mapped with the standard codes, and are stored and managed in the service-providing system.

Next, a process of implementing the second and third methods through the nurse web screen will be described.

At this time, FIGS. 4a to 4g illustrate management screens for standard nurse terms, and illustrate screen that can be used by an authorized manager other than general nurses (third example to which the method has been applied). That is, the screens shown in FIGS. 4a to 4g illustrate a dialog box on a web screen in which a manager can add, modify or delete standard nurse terms.

Figure 4A:
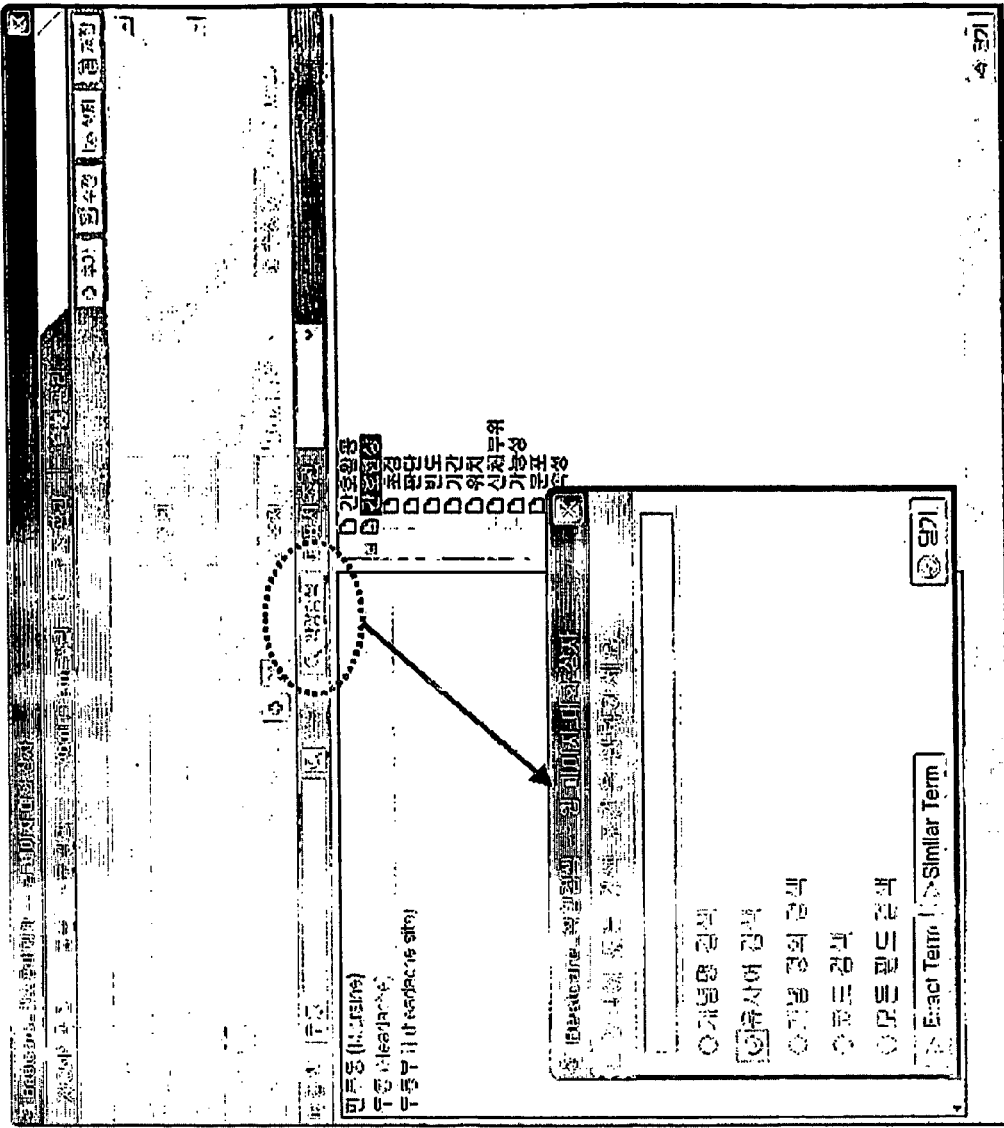
FIGS. 4a to 4h are diagrams illustrating various examples of a method for providing standard terms for a nurse through a nurse web screen in the method for computerizing and standardizing medical information according to the present invention.

First, FIG. 4a is a diagram illustrating an example of an ICNP management screen, and is a screen on which a nurse can map various standard nurse terms to the standard code (ICNP).

Figure 4B:
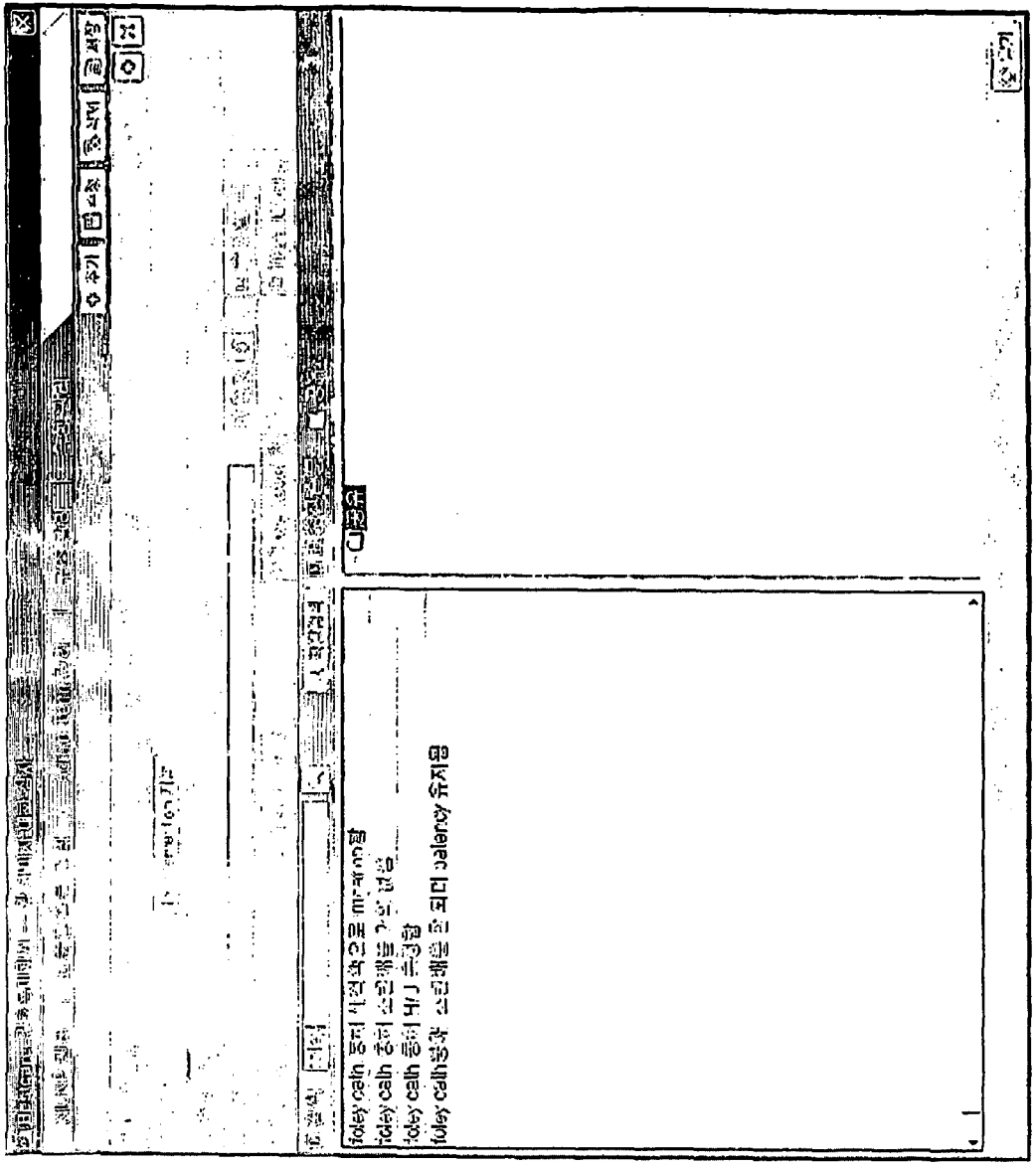

Next, FIG. 4b is a management screen for standard statement sentence (hereinafter, referred to as statement sentence used upon writing nursing statement sentences), i.e. a screen in which various standard statement sentences needed for the nurse to write a nursing diary may be combined and formed in advance. That is, FIG. 4b is a web screen on which the respective standard nurse terms are combined and formulated into one standard statement sentence form.

Figure 4C:
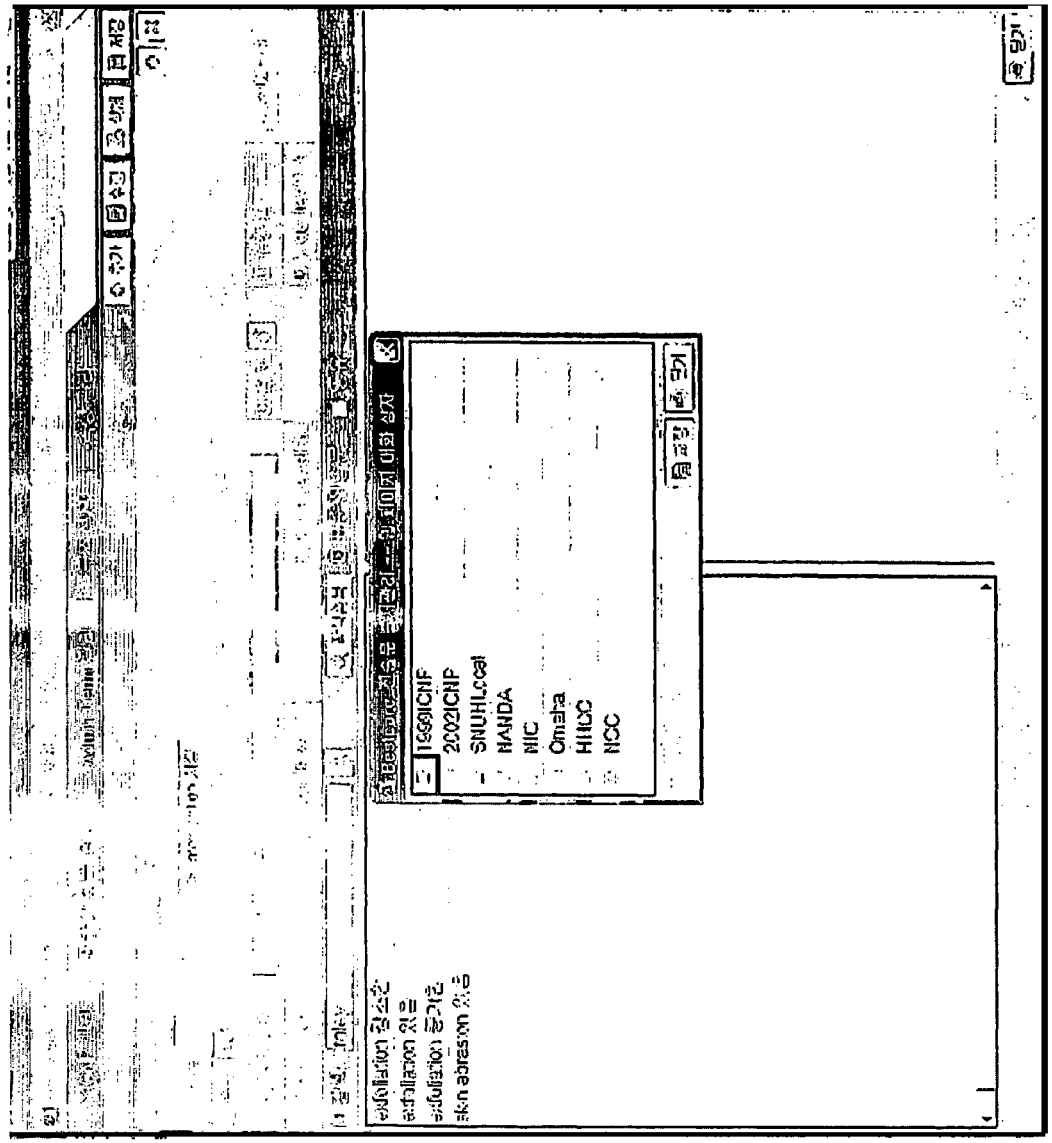

Next, FIG. 4c is a screen on which a nurse can inquire a basis of the standard statement sentence, and is a screen in which the basis of a standard statement sentence set up in FIG. 4b can be inquired.

Figure 4D:
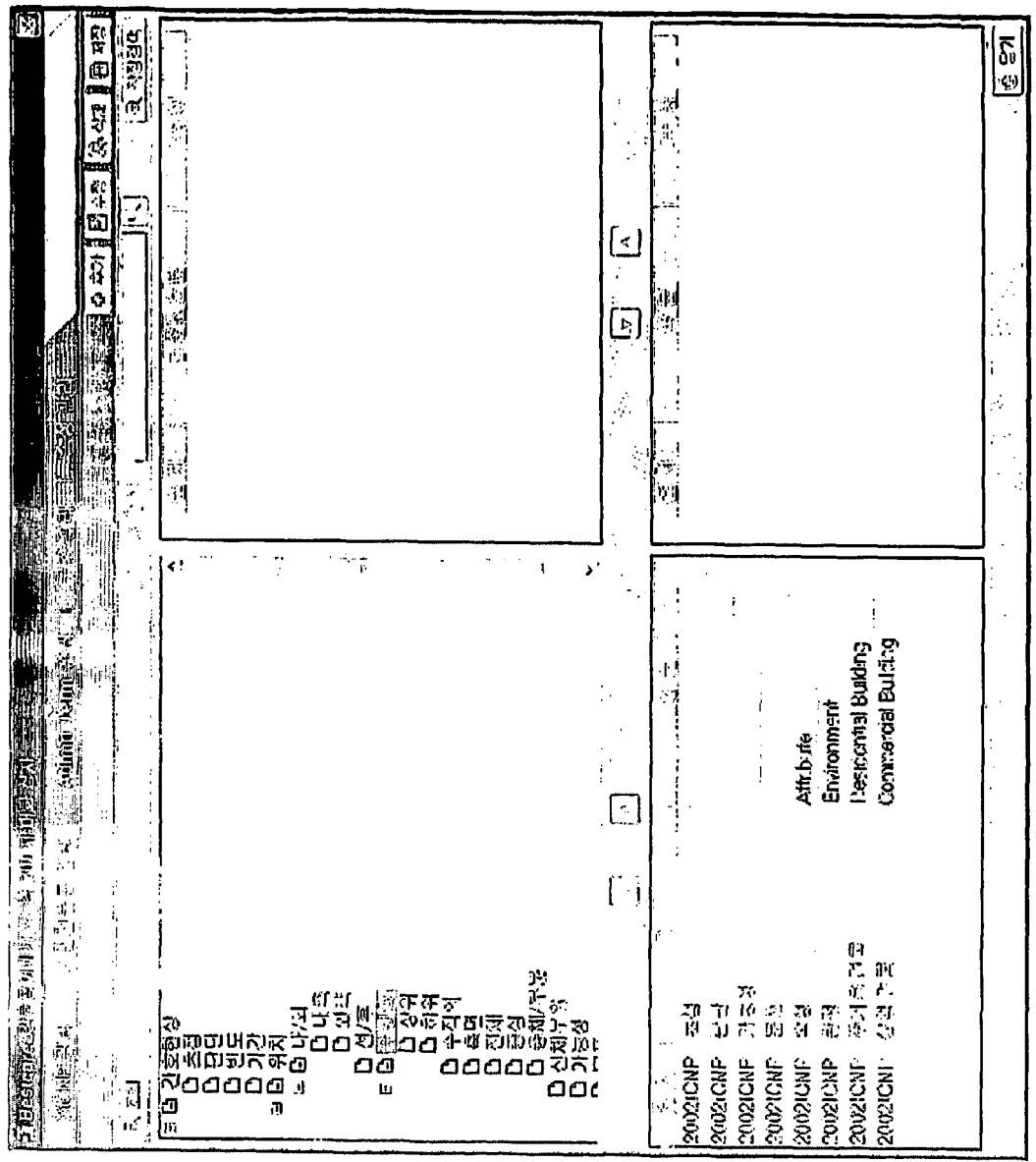
Figure 4E:
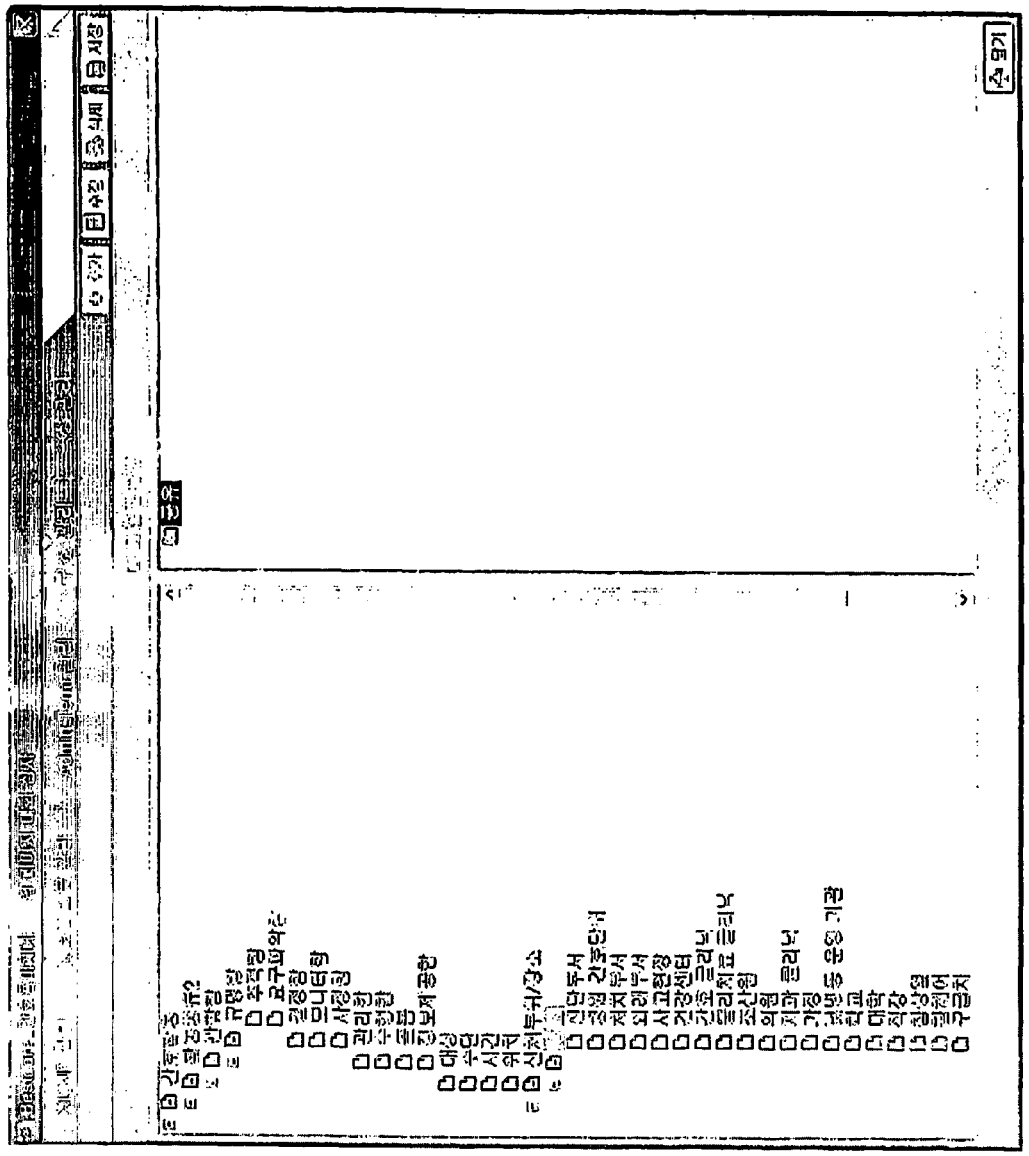

Next, FIG. 4d illustrates a screen on which a nurse defines and manages basic standard nurse terms, and FIG. 4e illustrates a screen on which a tree of a standard statement sentences can be managed.

Figure 4F:
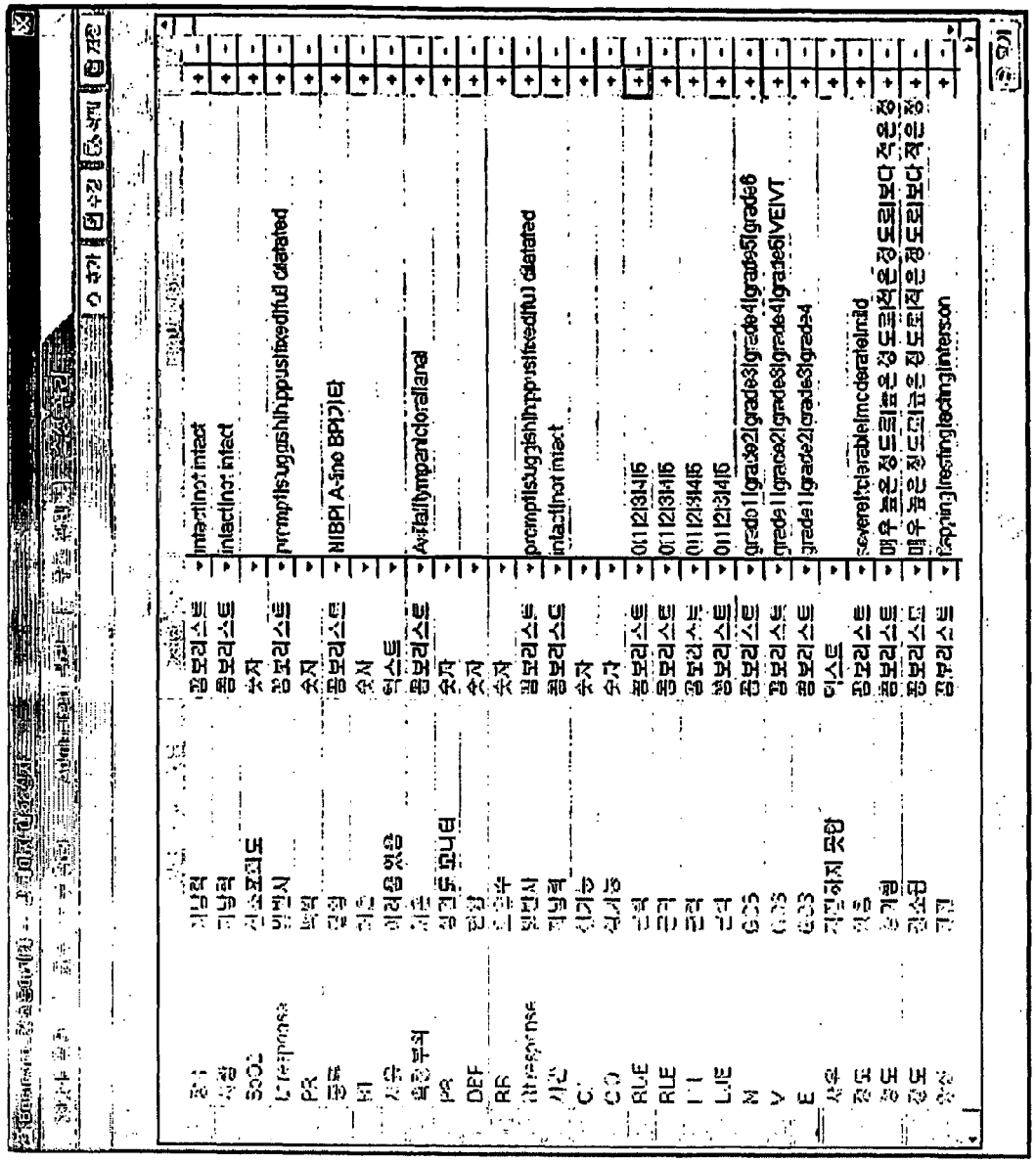
Figure 4G:
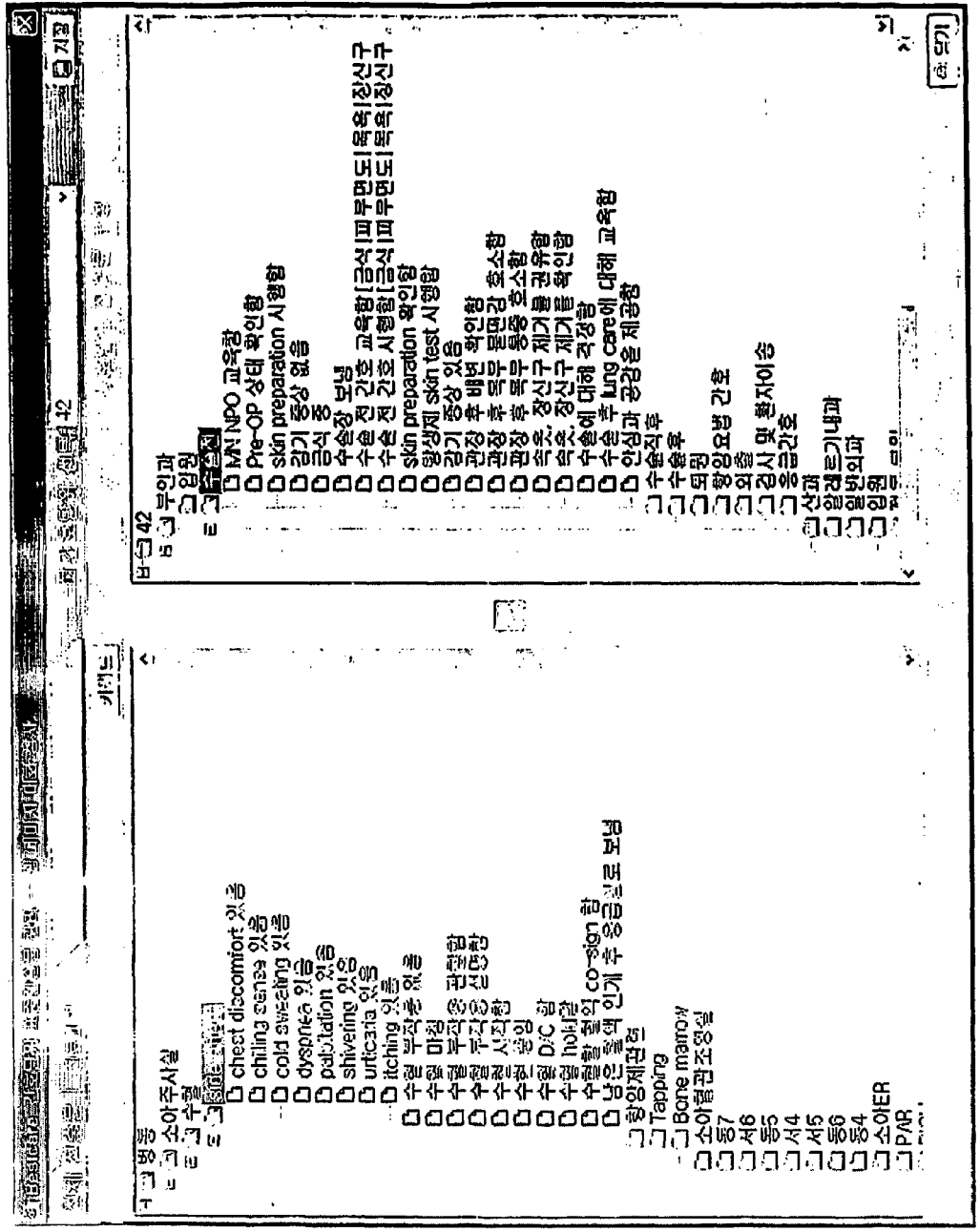

Next, FIG. 4f is a screen on which a nurse can manage an attribute connected to standard statement sentence, and FIG. 4g illustrates a screen on which statement sentences are formed and managed for each nursing unit.

Figure 4H:
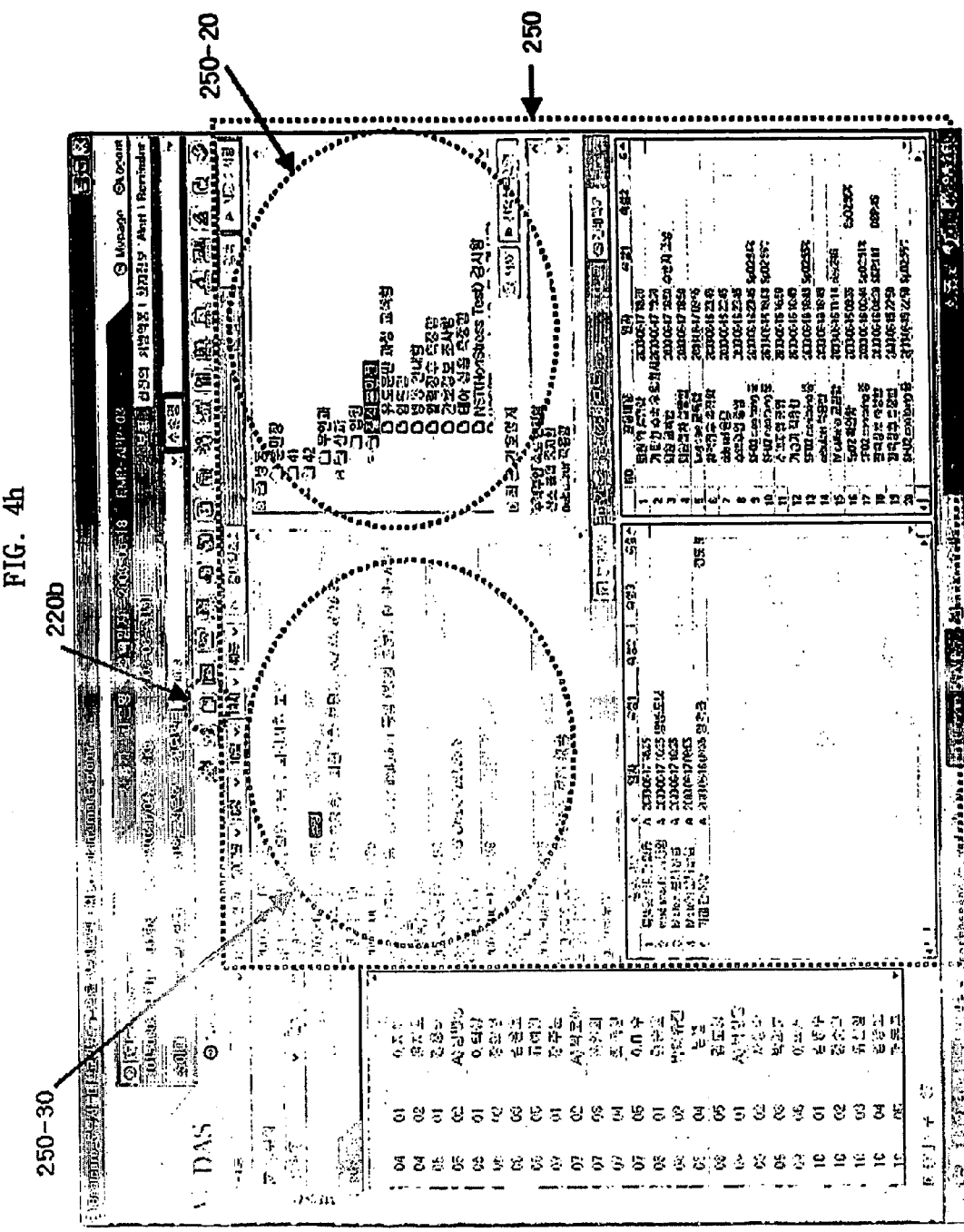

Finally, FIG. 4h illustrates a state in which a nurse inputs a nursing diary for patients in a nursing diary record column provided on a nurse web screen using the aforementioned standard statement sentences (an example in which the third method is applied).

That is, FIG. 4h illustrates a nurse web screen output on the nurse terminal 30 so that it can be used by general nurses, and particularly, a patient information input and output portion 250 on which on which a nursing diary for patients. That is, if the nurse selects a nursing diary shortcut icon 220b among a variety of menus provided through the web screen, the nursing diary input screen as shown in FIG. 4h is output, wherein a selection window 250-20 on which statement sentences created during nursing patients are output on the patient information input and output portion 250 for each date.

At this time, the nurse selects, clicks and stores on the selection window the standard statement sentence by which patient status can be represented, wherein the selected contents are displayed in the nursing diary column 250-30, transmitted to the patient information managing unit 13, stored along with other information regarding the patients. That is, the control unit 12 of the service-providing system 10 again selects and combines the aforementioned standard statement sentences, resulting in a nursing statement sentence. However, one selected standard statement sentence may be stored as a nursing statement sentence.

That is, the respective items output on the selection window 250-20 are statement sentences which are combined to standard terms standardized according to the aforementioned method, and is registered or managed through FIGS. 4a to 4g.

Meanwhile, users who are engaged in a medical industry will be able to more conveniently and accurately input and read information needed for treating and caring for patients as well as to standardize medical information currently used in a variety of representation manners home and abroad, by using the aforementioned method for computerizing and standardizing medical information according to the present invention.

The present invention is not limited to the aforementioned embodiments. A variety of variations and modifications may be made to the present invention by those skilled in the art, and are contained the spirit and scope of the present invention defined in appended claims.

INDUSTRIAL APPLICABILITY

The present invention has an excellent advantage that medical information currently used in a variety of representation manners both at home and abroad can be standardized as well as information needed upon medically examining and caring for patients can be input and read more conveniently and accurately.

Further, the present invention is applicable to a method for managing medical information implemented in doctor, nurse, and examination room staff terminals. Accordingly, doctor, nurse, and examination room staff can share examination, nursing, inspection and treatment results for patients over a network, thereby medically examining the patients more rapidly and accurately.

The invention claimed is:

1. A method, comprising:

displaying, using a processing device, standard patient-language symptoms on an interface of a display device as one of a selection item and a check item of a chief complaint field of a medical record; and using an input device to select or check one of the standard patient-language symptoms to enter the selected patient-language symptom in the chief complaint field so as to generate a new medical record that identifies the selected patient-language symptom as a chief complaint, wherein the standard patient-language symptoms are selected extracted patient-language terms used in existing medical records of patients regarding symptoms of the patients, and wherein the standard patient-language symptoms are accessed from a database which stores the standard patient-language symptoms so as to be free from association with any particular medical record, wherein the standard patient-language symptoms are normalized, the normalizing comprising, separating the standard patient-language symptoms according to each meaning, aligning the standard patient-language symptoms on a term spelling basis, restoring misspellings and abbreviations of standard patient-language symptoms to full spellings, and excluding ambiguous standard patient-language symptoms, wherein the standard patient-language symptoms are mapped to standard codes, and wherein the mapping comprises, imparting a concept identifier of a standard code to each of the standard patient-language symptoms, and classifying each of the standard patient-language symptoms according to whether a concept of the patient-language symptom exactly matches or does not exactly match the imparted concept identifier of the standard code, and when the standard patient-language symptom exactly matches the imparted concept identifier of the standard code, mapping the standard patient-language symptom to the imparted concept identifier, when the standard patient-language symptom does not exactly match the imparted concept identifier of the standard code, retrieving and mapping a concept that is similar or broader than the patient-language symptom, such that:

when a same spelling belongs to a variety of concepts, a most suitable concept for the character of the standard patient-language symptom among the concepts is retrieved and mapped, when two concepts are have the same parent in a parent-child relationship and a difference between the two concepts is ambiguous clinically, one concept is selected and mapped consistently, when the meaning of the standard patient-language symptom is subdivided into multiple concepts, a top concept capable of representing the comprehensive meaning of the standard patient-language symptom is mapped, when standard patient-language symptoms of the same concept and the same spelling have a duplicate concept status, a concept with a current status is mapped, and when a standard patient-language symptom is to be mapped to an overlapping or unclear concept, the mapping is performed only if no alternative concept for mapping is available.

2. The method of claim 1, wherein the database also stores selected terms regarding diagnosis names, operation names, terms used upon writing of the status of patients by nurses, terms used upon writing of the status of the patients by doctors, prescription terms used by doctors, and medicine terms.

3. The method of claim 2, further comprising using the input device to perform a standard statement sentence write function that combines the selected terms used upon writing of the status of patients by nurses into a standard statement sentence used to write a medical record.

4. The method of claim 1, wherein the displaying further comprises displaying the standard patient-language symptoms as selection items applicable to writing of a sentence in the medical record.

5. The method of claim 1, further comprising using the input device to modify, delete, or add to the standard patient-language symptoms in the database.

6. The method of claim 1, further comprising communicating over a network with a doctor terminal, a nurse terminal, an examination room staff terminal, and a general medical affairs terminal to perform the displaying.

7. The method of claim 1, wherein the selected extracted patient-language terms are from discharge summaries.

8. The method of claim 1, wherein the selected extracted patient-language terms are separated into main concepts, concept qualifiers, and concept modifiers.

9. The method of claim 8, wherein the main concepts are aligned on a spelling and concept basis.

10. A tangible computer-readable medium having stored thereon, computer-executable instructions that, if executed by a computing device, cause the computing device to perform a method comprising:

displaying standard patient-language symptoms on an interface of a display device as one of a selection item and a check item of a chief complaint field of a medical record; and selecting or checking one of the standard patient-language symptoms to enter the selected patient-language symptom in the chief complaint field so as to generate a new medical record that identifies the selected patient-language symptom as a chief complaint, wherein the standard patient-language symptoms are selected extracted patient-language terms used in existing medical records of patients regarding symptoms of the patients, and wherein the standard patient-language symptoms are accessed from a database which stores the standard patient-language symptoms so as to be free from association with any particular medical record, wherein the standard patient-language symptoms are normalized, the normalizing comprising, separating the standard patient-language symptoms according to each meaning, aligning the standard patient-language symptoms on a term spelling basis, restoring misspellings and abbreviations of standard patient-language symptoms to full spellings, and excluding ambiguous standard patient-language symptoms, wherein the standard patient-language symptoms are mapped to standard codes, wherein the mapping comprises,
    imparting a concept identifier of a standard code to each of the standard patient-language symptoms, and
    classifying each of the standard patient-language symptoms according to whether a concept of the patient-language symptom exactly matches or does not exactly match the imparted concept identifier of the standard code, and
    when the standard patient-language symptom exactly matches the imparted concept identifier of the standard code, mapping the standard patient-language symptom to the imparted concept identifier,
    when the standard patient-language symptom does not exactly match the imparted concept identifier of the standard code, retrieving and mapping a concept that is similar or broader than the patient-language symptom, such that when a same spelling belongs to a variety of concepts, a most suitable concept for the character of the standard patient-language symptom among the concepts is retrieved and mapped, such that:
        when a same spelling belongs to a variety of concepts, a most suitable concept for the character of the standard patient-language symptom among the concepts is retrieved and mapped,
    when two concepts are have the same parent in a parent-child relationship and a difference between the two concepts is ambiguous clinically, one concept is selected and mapped consistently,
    when the meaning of the standard patient-language symptom is subdivided into multiple concepts, a top concept capable of representing the comprehensive meaning of the standard patient-language symptom is mapped,
    when standard patient-language symptoms of the same concept and the same spelling have a duplicate conceit status a concept with a current status is mapped, and
    when a standard patient-language symptom is to be mapped to an overlapping or unclear concept, the mapping is performed only if no alternative concept for mapping is available.

* * * * *